US010264993B2

(12) United States Patent
Looney et al.

(10) Patent No.: US 10,264,993 B2
(45) Date of Patent: Apr. 23, 2019

(54) SAMPLE SCANNING AND ANALYSIS SYSTEM AND METHODS FOR USING THE SAME

(75) Inventors: Erin Claude Looney, Reno, NV (US); David James Harra, San Francisco, CA (US)

(73) Assignee: RF SCIENCE & TECHNOLOGY INC., Reno, NV (US)

( * ) Notice: Subject to any disclaimer, the term of this patent is extended or adjusted under 35 U.S.C. 154(b) by 1764 days.

(21) Appl. No.: 11/821,481

(22) Filed: Jun. 21, 2007

(65) Prior Publication Data

US 2008/0319293 A1    Dec. 25, 2008

(51) Int. Cl.
*G01N 33/48* (2006.01)
*G01N 33/50* (2006.01)
*A61B 5/05* (2006.01)
*G06F 19/00* (2018.01)
*A61B 5/145* (2006.01)
*A61B 5/00* (2006.01)
*G06F 19/12* (2011.01)

(52) U.S. Cl.
CPC .............. *A61B 5/05* (2013.01); *A61B 5/0507* (2013.01); *A61B 5/14532* (2013.01); *A61B 5/411* (2013.01); *G06F 19/701* (2013.01); *G06F 19/12* (2013.01)

(58) Field of Classification Search
None
See application file for complete search history.

(56) References Cited

U.S. PATENT DOCUMENTS

| | | |
|---|---|---|
| 3,768,054 A | 10/1973 | Neugebauer |
| 4,428,366 A | 1/1984 | Findl et al. |
| 4,582,985 A | 4/1986 | Lofberg |
| 4,633,179 A * | 12/1986 | Sugimoto ............... 324/309 |
| 4,672,346 A | 6/1987 | Miyamoto et al. |
| 4,679,426 A | 7/1987 | Fuller |
| 4,765,179 A | 8/1988 | Fuller |
| 4,801,209 A | 1/1989 | Wadlow |
| 4,875,486 A | 10/1989 | Rapoport |
| 4,899,109 A * | 2/1990 | Tropp et al. ............ 324/320 |
| 4,975,581 A | 12/1990 | Robinson et al. |
| 4,993,068 A | 2/1991 | Piosenka et al. |
| 5,050,607 A | 9/1991 | Bradley et al. |
| 5,063,934 A | 11/1991 | Rapoport et al. |
| 5,072,732 A | 12/1991 | Rapoport et al. |
| 5,173,661 A * | 12/1992 | Knuttel et al. ........... 324/309 |
| 5,320,103 A | 6/1994 | Rapoport et al. |
| 5,328,822 A | 7/1994 | McKinney et al. |
| 5,348,002 A | 9/1994 | Caro |
| 5,363,052 A | 11/1994 | McKee |
| 5,372,136 A | 12/1994 | Steuer |
| 5,411,023 A | 5/1995 | Morris, Sr. et al. |
| 5,415,163 A | 5/1995 | Harms |
| 5,435,169 A | 7/1995 | Mitra |
| 5,462,054 A | 10/1995 | Rapoport et al. |
| 5,487,870 A | 1/1996 | McKinney et al. |
| 5,508,203 A | 4/1996 | Fuller |
| 5,565,834 A | 10/1996 | Hanley et al. |
| 5,575,977 A | 11/1996 | McKinney et al. |
| 5,592,086 A | 1/1997 | Weinstock et al. |
| 5,626,137 A | 5/1997 | Dumoulin et al. |
| 5,680,460 A | 10/1997 | Tomko et al. |
| 5,744,958 A | 4/1998 | Werne |
| 5,792,668 A | 8/1998 | Fuller |
| 5,894,221 A | 4/1999 | Watanabe et al. |
| 6,011,858 A | 1/2000 | Stock et al. |
| 6,016,476 A | 1/2000 | Maes et al. |
| 6,035,398 A | 3/2000 | Bjorn |
| 6,038,666 A | 3/2000 | Hsu et al. |
| 6,043,881 A | 3/2000 | Wegrzyn et al. |
| 6,110,660 A | 4/2000 | Kriz et al. |
| 6,061,587 A | 5/2000 | Kucharczyk et al. |
| 6,107,627 A | 8/2000 | Nakagawa et al. |
| 6,147,490 A | 11/2000 | Watanabe |
| 6,184,684 B1 | 2/2001 | Dumoulin et al. |
| 6,263,228 B1 | 7/2001 | Zhang et al. |
| 6,309,884 B1 | 10/2001 | Cooper et al. |
| 6,411,093 B2 * | 6/2002 | Schwilch et al. ............ 324/322 |
| 6,477,398 B1 | 11/2002 | Mills |
| 6,480,141 B1 | 11/2002 | Toth et al. |
| 6,529,617 B1 | 3/2003 | Prokoski |
| 6,614,238 B1 | 9/2003 | Jean et al. |
| 6,723,048 B2 | 4/2004 | Fuller |
| 6,780,378 B2 | 8/2004 | Abbasi et al. |

(Continued)

FOREIGN PATENT DOCUMENTS

EP    0350546 A2    1/1990
FR    2562785    10/1985

(Continued)

OTHER PUBLICATIONS

Shim Coils, 2011. Dorland's Illustrated Medical Dictionary, 2 pages. Retrieved online on Mar. 31, 2013 from «http://www.credoreference.com».*

(Continued)

*Primary Examiner* — Russell S Negin

(57) ABSTRACT

A system and methods for scanning and analyzing one or more characteristics of a sample utilizing electromagnetic radiation is described. More particularly, the system and methods utilize an electromagnetic radiation source connected to a transmitter and an analyzer connected to a receiver. A sample to be analyzed is placed between the transmitter and receiver and a frequency sweep of electromagnetic radiation is transmitted through the sample to create a series of spectral data sets, which are developed into a composite spectrogram by the analyzer and processed to determine one or more characteristics of the sample. A magnetic field can alternatively be applied around the transmitter, receiver and sample to enhance some characteristic analysis applications and to make other characteristic analysis applications possible. Samples include inert and living items and the characteristics include a wide variety of different applications. Although pattern recognition is utilized in some applications to match a present composite spectrogram with previously detected spectrograms, the present composite spectrogram can also be analyzed based on pattern components to make characteristic determinations without per-use calibration and without utilizing any pattern matching.

112 Claims, 12 Drawing Sheets

(56) References Cited

U.S. PATENT DOCUMENTS

| | | | |
|---|---|---|---|
| 6,862,466 | B2 | 3/2005 | Ackerman |
| 6,864,826 | B1 | 3/2005 | Stove |
| 6,987,393 | B2 | 1/2006 | Jean et al. |
| 6,995,558 | B2 | 2/2006 | Butters et al. |
| 7,081,747 | B2 | 7/2006 | Butters et al. |
| 7,184,810 | B2 | 2/2007 | Caduff |
| 7,221,169 | B2 | 5/2007 | Jean et al. |
| 7,228,163 | B2 | 6/2007 | Ackerman |
| 7,315,767 | B2 | 1/2008 | Caduff et al. |
| 7,316,649 | B2 | 1/2008 | Fuller |
| 7,347,365 | B2 | 3/2008 | Rowe |
| 7,349,556 | B2 | 3/2008 | Brooks |
| 7,449,695 | B2 | 11/2008 | Zidmars et al. |
| 7,685,433 | B2 | 3/2010 | Mantyjarvi et al. |
| 7,705,988 | B2 | 4/2010 | Richman |
| 7,781,736 | B2 | 8/2010 | Logan, Jr. et al. |
| 8,259,299 | B2 * | 9/2012 | Harra et al. .................. 356/437 |
| 8,382,668 | B2 * | 2/2013 | Harra et al. .................. 600/365 |
| 2002/0009213 | A1 | 1/2002 | Rowe et al. |
| 2003/0083563 | A1 | 5/2003 | Katsman et al. |
| 2003/0128867 | A1 | 7/2003 | Bennett |
| 2003/0133596 | A1 | 7/2003 | Brooks |
| 2004/0147819 | A1 | 7/2004 | Caduff et al. |
| 2004/0220749 | A1 * | 11/2004 | Miller et al. .................... 702/19 |
| 2005/0090726 | A1 | 4/2005 | Ackerman |
| 2005/0113650 | A1 | 5/2005 | Pacione et al. |
| 2005/0269412 | A1 | 12/2005 | Chiu et al. |
| 2006/0080551 | A1 | 4/2006 | Mantyjarvi et al. |
| 2007/0237365 | A1 | 10/2007 | Monro |
| 2007/0255141 | A1 | 11/2007 | Esenaliev et al. |
| 2007/0290800 | A1 | 12/2007 | Fuller |
| 2008/0057526 | A1 | 3/2008 | Caduff et al. |
| 2008/0192988 | A1 | 8/2008 | Uludag et al. |
| 2008/0319293 | A1 | 12/2008 | Looney et al. |
| 2009/0156915 | A1 | 6/2009 | Cross |

FOREIGN PATENT DOCUMENTS

| | | |
|---|---|---|
| GB | 1360606 A | 7/1974 |
| JP | 56014145 | 2/1981 |
| WO | 9932897 A | 7/1999 |
| WO | 0147415 A1 | 7/2001 |
| WO | 2008156787 | 12/2008 |
| WO | WO 2010/059744 | 5/2010 |

OTHER PUBLICATIONS

Nuclear Magnetic Resonance (NMR) 2014. In M. Clugston, The Penguin Dictionary of Science. London, United Kingdom: Penguin. Retrieved online from «http://www.credoreference.com».*

Active Spectrum, Inc., "What is Electron Spin Resonance (ESR)?", website http://www.activespectrum.com/about.html, available at least by Jul. 30, 2009.

Gulich et al., "Dielectric spectroscopy on aqueous electrolytic solutions", Radiat Environ Biophys 48, pp. 107-114, 2009.

Gilbert et al., "Kinetic EPR studies of the addition of carbohydrate-derived radicals to methacrylic acid", J. Chem. Soc., Perkin Trans. 2, pp. 1565-1572, 1998.

Mathur et al., "Dielectric Spectroscopy: Choosing the Right Approach", website http://license.icopyright.net/user/viewFreeUse.act?fuid=Njc0MDkzOA%3D%3D, PharmTech.com. Sep. 2008. Available at least by Jan. 9, 2010.

Feldman et al., "Time domain dielectric spectroscopy. A new effective tool for physical chemistry investigation", Colloid and Polymer Science, vol. 270, pp. 768-780, 1992.

Fruhstorfer, Heinrich, Heinrich, "Frequent lancing for monitoring blood glucose may cause skin changes", Pract Diab Int vol. 23 No. 5, Marburg, Germany, Jun. 2006.

Gottman et al., "Self-Monitoring Effects in a Program for Potential High School Dropouts: A Time-Series Analysis", Journal of Consulting and Clinical Psychology, vol. 39, No. 2, pp. 273-281, 1972.

Baker, et al., "Self-Monitoring May Be Necessary for Successful Weight Control", Behavior Therapy 24, pp. 377-394, 1993.

Schnoll, et al., "Self-regulation training enhances dietary self-efficacy and dietary fiber consumption", Journal of the American Dietetic Association, vol. 101, No. 9, pp. 1006-1011, Sep. 2001.

Kopelman, Peter G., "Obesity as a medical problem", Nature, vol. 404, pp. 635-643, Apr. 2000.

Pendi Existin Website, Including Technology, Presentations, Slide Show I: Medical Uses for RMM, Slide Show II: Personal Security With RMM, and All Related Materials at www.pindi.com, downloaded Apr. 19, 2007.

Active Spectrum, "What is Electron Spin Resonance (ESR)?", Internet website download, www.activespectrum.com/about.html, 3 pages, Copyrighted 2007 by Active Spectrum, Inc.

Wikipedia, "Electron Paramagnetic Resonance", Internet website download, www.en.wikipedia.org/Electron_spin_resonance, 9 pages, available at least by Aug. 12, 2009.

A. Poor, "On the Light Side: Security is All in Vein", Internet website download Aug. 11, 2009, http://www.ecnmag.com/Lightside-Security-All-in-Vein-011609.aspx, article published Feb. 2, 2009, 1 page.

M. Pene, "Baylor Researcher Creates New Way to Test Blood-Sugar Level", article published Feb. 18, 2008, Internet website download, www.baylor.edu/pr/news.php?action=story&story=49271, 1 page, available at least by Aug. 11, 2009.

Falco et al., "Approaching the Inverse Problem of the Multi-Layer Skin System", Solianis Monitoring AG and Applied Physics Dept., The Hebrew University of Jerusalem, 2008, Abstract only.

Caduff et al., "Non-invasive Glucose Monitoring in Patients with Type 1 Diabetes: Repeatability in the Same Subjects", R&D, Solianis Monitoring, Seminar for Statistics, Centre for clinical research, University Hospital Zurich, Clinic for Endocrinology and Diabetes, University Hospital Zurich and Research, Profil Institute for Metabolic Research, 2008, Abstract only.

Caduff et al., "Testing a Multisensor Concept under Simulated Home Use Conditions for non invasive Glucose Monitoring", Solianis Monitoring AG, Centre for clinical research, University Hospital Zurich, Clinic for Endocrinology and Diabetes, University Hospital Zurich and Seminar for Statistics, ETH Zurich, 2008, Abstract only.

Livshits et al. "The Study of the Dielectric Response of Red Blood Cells to Sugar Exposure—In vitro Basis for Non-invasive Glucose Impedance Monitoring", Department of Applied Physics, The Hebrew University of Jerusalem and Solianis Monitoring AG, 2005.

Huber et al., "The Compensation of Perturbation Effects in Glucose Monitoring Technologies Based on Impedance Spectroscopy", Solianis Monitoring, Swiss Federal Laboratories for Materials Testing and Research, Cantonal Hospital of St. Gallen and Institute for Clinical Research and Development, 2008.

Smith, J.L., "The Pursuit of Non-Invasive Glucose: "Hunting the Deceitful Turkey"", Seminal Book, Copyrighted 2006.

Caduff et al., "Non Invasive Glucose Monitoring—Next steps in an approach to address perturbing effects in an IS based monitoring technique", ADA Abstract 2006 Solianis. 2006.

Caduff et al., "Variations in Blood Glucose and their Impact on Various Blood Parameters in Healthy Subjects", DTM, Solianis Monitoring and Profil Inst. for Metabolic Research, 2006.

Talary et al., "Biological Application of Impedance Spectroscopy for in vivo Life Sign and Non Invasive Glucose Monitoring", Biodielectrics, Solianis Monitoring AG, 2006, 1 page.

Livshits et al., "The Study of the Dielectric Response of Red Blood Cells to Sugar Exposure—In vitro Basis for Non-invasive Glucose Impedance Monitoring", Department of Applied Physics, The Hebrew University of Jerusalem and Solianis Monitoring AG, 2005, 1 page.

Active Spectrum, Inc., "Benchtop Micro-ESR", Product Literature, available no earlier than 2005, 2 pages.

H.Westerhoff, R. Astumian, & D. Kell, "Mechanisms for the Interaction Between NonStationary Electric Fields and Biological Systems, II. Nonlinear Dielectric Theory and Free-Energy Transduction", Ferroelectrics, vol 86, 1988, pp. 79-101.

J. Liszi, E. Papp, & I. Ruff, "Field-dependent Kirkwood Factor in the Non-Linear Dielectric Behaviour of Binary Liquide Mixtures", J. Chem Soc., Faraday Trans. 1, 1982, vol. 78, pp. 915-922.

(56) References Cited

OTHER PUBLICATIONS

T. Furukawa, K. Nakajima, T. Koizumi, & M. Date, "Measurements of Nonlinear Dielectricity in Ferroelectric Polymers", Japanese Journal of Applied Physics, vol. 26, No. 7, Jul. 1987, pp. 1039-1045.
Author Unknown, "RealStream technology related to industrial analysis application", Excerpt from www.yet2.com, © 1999-2012 by yet2.com, Inc., 1 page.

* cited by examiner

SAMPLE SCANNING AND ANALYSIS SYSTEM AND METHODS FOR USING THE SAME

BRIEF DESCRIPTION OF THE INVENTION

The present invention is related to systems and methods for scanning and analyzing one or more characteristics of a sample utilizing electromagnetic radiation. More particularly, the systems and methods utilize an electromagnetic radiation source connected to a transmitter and an analyzer connected to a receiver. A sample to be analyzed is placed between the transmitter and receiver and a frequency sweep of electromagnetic radiation is transmitted through the sample to create a series of spectral data sets, which are developed into a composite spectrogram by the analyzer and processed to determine the one or more characteristics of the sample. A magnetic field can alternatively be applied around the transmitter, receiver and sample to enhance some characteristic analysis applications and to make other characteristic analysis applications possible. Samples include inert and living items and the characteristics include a wide variety of different applications. Although pattern recognition is utilized in some applications to match a present composite spectrogram with a previously detected spectrogram, the present composite spectrogram can also be analyzed based on pattern components to make characteristic determinations without per-use calibration and without utilizing any pattern matching.

CROSS-REFERENCES TO RELATED APPLICATIONS

Not Applicable.

STATEMENT AS TO THE RIGHTS TO INVENTIONS MADE UNDER FEDERALLY SPONSORED RESEARCH OR DEVELOPMENT

Not Applicable.

REFERENCE TO A "SEQUENCE LISTING," A TABLE, OR A COMPUTER PROGRAM LISTING APPENDIX SUBMITTED ON A COMPACT DISK

Not Applicable.

BACKGROUND OF THE INVENTION

Electromagnetic radiation has been used in a wide array of noninvasive diagnostic applications. X-rays have been used for many years to create a two dimensional image of the inside of an object. Computed axial tomography scanners are able to generate three dimensional images from a series of two dimensional x-ray images. Magnetic resonance imaging (also known as nuclear magnetic resonance spectroscopy), such as disclosed in Harms et al., U.S. Pat. No. 5,415,163 A and Rapoport et al., U.S. Pat. No. 4,875,486 A, operate by first applying a magnetic field to a subject so as to align, in a uniform manner, the nuclei of atoms within a portion of the subject to be tested. These aligned nuclei are then briefly exposed to a radio frequency (RF) signal set to a specific frequency, which causes each of the various aligned nuclei at a lower energy state to spin or flip to a higher energy state, known as a resonant frequency. The magnetic field is then removed or altered, causing the nuclei forced to a resonant frequency to become unstable and return to their original lower energy state. This later process is called spin relaxation. The faint energy released from the spin relaxation is then collected as a representation of the nuclei within the sample.

Hence, the spin relaxation energy released by the sample is used to generate an image that is representative of the sample. The RF signal itself is not utilized for detection or imaging purposes—it is only used to excite the nuclei to a higher energy state and is removed before the spin relaxation energy is detected. Further, the magnetic field(s) are only used to align and then release the nuclei in the sample, and are removed or altered before spin relaxation can occur.

While electromagnetic signals transmitted through a specimen have been used to detect or measure the concentration of various chemicals in that specimen, such prior techniques were not highly accurate and results were often difficult to repeat. For example, U.S. Pat. No. 4,679,426 disclosed a non-invasive technique for measuring the concentration of chemicals, such as sodium chloride, in a sample. Periodic electromagnetic waves between 10 MHz and 100 MHz were coupled to a subject's finger and resulting waveforms were found to be indicative, at specific frequencies (i.e., 17.75 MHz for sodium chloride and potassium chloride), of concentration levels of those chemicals in the finger. Likewise, U.S. Pat. No. 4,765,179 used periodic electromagnetic waves between 1 MHz and 1 GHz, that were coupled to a subject's finger, to generate a waveform that provided meaningful analysis of glucose levels in the subject based on the presence of other compounds in the subject's blood at specific frequencies (i.e., 17.75 MHz for sodium chloride and potassium chloride, 11.5 MHz for ethyl alcohol, etc.).

In U.S. Pat. No. 5,508,203 (the "'203 patent"), high frequency electromagnetic radiation was coupled to a specimen through a probe pair to generate a signal of varying amplitude or phase that could be compared to a source signal to determine the presence of a target chemical, such as NaCl, to help determine glucose levels. While this later technique represented an improvement over the prior methods, it was soon realized that electrolytes, e.g., NaCl, KCl, $Na_2HPO_4$, and $KH_2PO_4$ of varying concentrations in human blood, can affect the accuracy of glucose measurements using the '203 patent.

To account for the deficiencies in the '203 patent, a new technique was developed in U.S. Pat. No. 5,792,668 (the "'668 patent"), in which two signals were transmitted through the subject at the same time and the magnitude of impedance at the subject was measured to determine a glucose level in the subject. In particular, the two signals had a cross-over frequency of about 2.5 GHz that provided the best measurement of impedance. In blood specimens, it was found that electrolyte concentration effects are effectively "tuned out" by examining impedance at this cross-over frequency. A similar approach was applied in U.S. Pat. No. 7,184,810 (the "'810 patent"), which cites the '668 patent. In the '810 patent, a probe is applied to the subject's skin, through which electric pulses from a pulse generator are fed and partially reflected back to a measuring device, where a time resolved measurement is made. The glucose level is determined from matching the measured voltage to a calibration table.

The next evolutionary step in the development of electromagnetic energy signals to determine the presence and concentration level of chemicals within a subject is represented in U.S. Pat. No. 6,723,048 B2 (the "'048 patent"), which is assigned to the assignees of the present application and which discloses a noninvasive apparatus for analyzing blood glucose and similar characteristics. The '048 patent apparatus utilizes spaced apart transmission and detection nodes placed on either side of and in contact with a sample to be tested. The nodes are always in close proximity to one or more pairs of magnets that create a magnetic field that envelopes the nodes and the sample between the nodes. An RF signal having a frequency between 2 GHz and 3 GHz is transmitted from the transmission node through the sample and to the detection node.

The detected signal is then sent to an analyzer that employs pattern recognition techniques to compare the detected signal at a specific frequency (with respect to glucose, the '048 patent specified 2.48 GHz), to previously detected signals at the same frequency to make a determination regarding the characteristic of the sample being tested. For example, if the sample was a finger of a patient that had previously been tested when the patient was known to have different glucose levels (verified through a more traditional form of glucose testing) to create three or more previously detected signal patterns, the presently detected signal would be compared to each of these previously detected signal patterns to determine which pattern it most closely resembled in order to approximate the patient's present blood glucose level.

In addition to testing glucose levels and other blood chemistries, it has been speculated that electromagnetic frequency spectrum technologies could have application to the biometric identification field, but no reliable technique has been developed for this purpose. In many fields of activity, it is essential that persons be identified or their claimed identity be authenticated. Examples of such fields include granting physical access or entry into buildings, rooms or other spaces, airport security, credit card purchasers, ATM users, passport verification, electronic access to information or communication systems, etc.

A number of noninvasive detection technologies have been developed to address these needs, such as fingerprint scans, iris and retina scans, and voice recognition. These technologies operate on the principal that individuals possess unique and unchanging physical characteristics that can be measured and compared with stored data. The basic requirements for acceptable biometric technology are that it must allow for practical widespread use, be accurate and reliable, be difficult or impossible to circumvent, be quick, easy and convenient, present no or little privacy violation concerns, be low cost to produce, and be consumer friendly. Current biometric identification and authentication technologies do not meet all of these basic requirements.

Iris and retina scanning technologies can be highly accurate, but the equipment used in scanning is expensive and requires substantial space. Further, humans are highly uncomfortable with the idea of having their eyes scanned with a laser or infrared light or having their picture taken and stored by a machine (and then used by who knows who). Also, iris and retina scanners have been spoofed with a number of techniques that have required the technologies to be modified in various ways, making the technology more expensive, less convenient, and less consumer friendly.

Electronic or optical fingerprint scanning systems are inexpensive, but are not very accurate, are easily damaged, and can be easily spoofed. Variations in skin, ethnic races with very light fingerprint patterns, people with unusually dry skin, elderly people, people with rough hands, water webbing, abrasions and cuts have all been known to create difficulties for fingerprint systems. Furthermore, many people consider fingerprinting to be an invasion of their privacy because of the heavy use of fingerprinting for law enforcement purposes. Additionally, many fingerprint scanning devices have been easily spoofed with objects as common as gummy candy.

Voice recognition systems tend to be the least accurate of the other biometric identification and authentication technologies. Voices can be readily recorded or mimicked, and allergies, colds and other respiratory issues can readily produce false negatives. Hand geometry and face recognition systems suffer from similar issues. They also tend to require a large amount of space and face recognition systems can be expensive. As with fingerprints, changes in a subject's skin, such as a suntan, a burn or a skin condition, or other changes to a subject's physical appearance can present problems for the system.

DETAILED DESCRIPTION OF THE INVENTION

Figure 1:
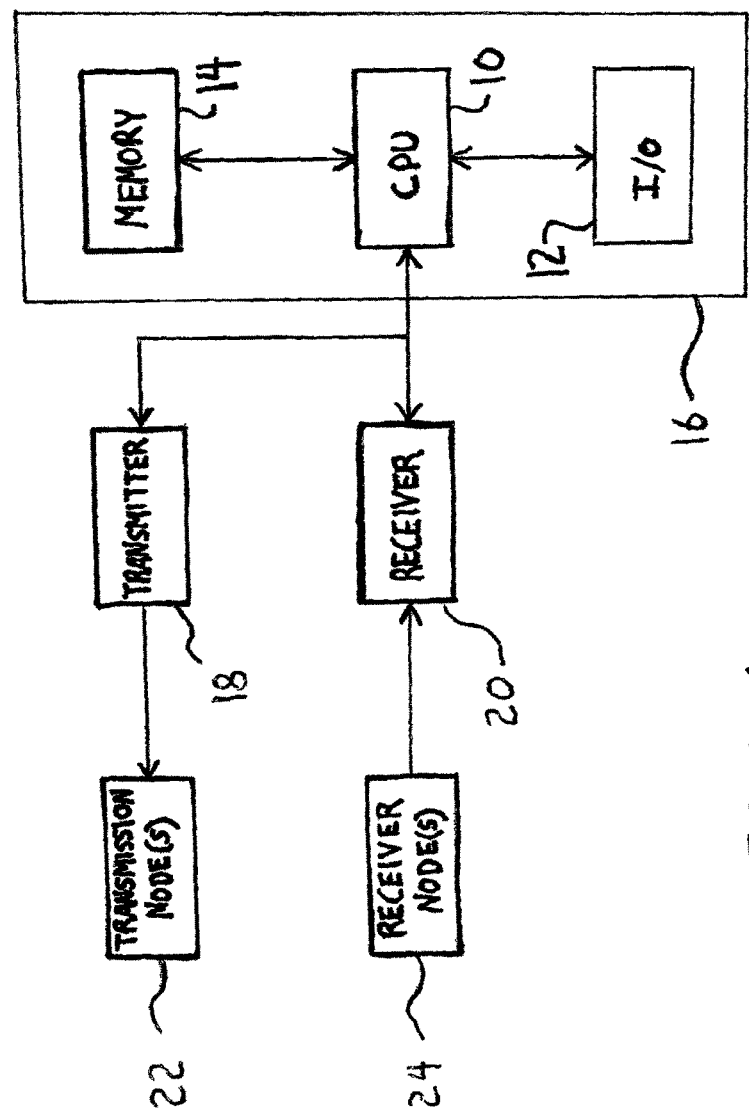
FIG. 1 is a block diagram illustrating the transmission, reception and analysis systems of the present invention.

The present invention is related to noninvasive systems and methods for scanning and analyzing one or more characteristics of a sample, including living and inert objects, utilizing electromagnetic radiation. In particular, the present invention utilizes a large spectrum of electromagnetic radiation that is transmitted through a sample to a receiver that creates a series of spectral data sets that are then developed into a composite spectrogram by an analyzer and processed to determine the one or more characteristics of the sample. A magnetic field can alternatively be applied around the transmitter, receiver and sample to enhance some characteristic analysis applications and to make other characteristic analysis applications possible. With respect to humans, the sample is usually a finger or some other part of the body that can be inserted into or placed on a scanning apparatus for scanning purposes.

While a characteristic can be the sample's possession of some substance, feature, level, percentage, sui generis identity, etc., a characteristic could also be a class, species, genre or category. In other words, a characteristic could be almost anything. The characteristics that can be tested or scanned for in humans and many other living samples include naturally occurring components of the blood, such as blood glucose levels, hemoglobin, cholesterol levels, proteins, red and white blood cell counts, lipids, C-reactive proteins, calcifications and hormone levels, as well as introduced components, such as steroids, pathogens, viruses, bacteria, yeasts and heavy metals, as well as many other biological markers, agents and substances, including biometric identifying markers and controlled substances such as illegal drugs, alcohol and poisons. For agricultural inspection purposes, meat and produce can be tested for characteristics indicating bacterial and other forms of contamination. In food processing operations, food products can be tested to regulate mixtures or the quantity of ingredients present, as well as to detect the presence of foreign elements such as metal, blood, nuts, milk and other allergens.

In security applications, unknown substances can be tested to determine their identity, such as illegal drugs, prescription drugs, explosives, poisons and bacterial agents (e.g., anthrax, nerve agents, etc.). Similarly, environmental substances can be scanned and identified in a wide variety of other applications, including biohazard and hazardous material situations, analysis of drinking water for pollutants, contaminants, minerals, and bacteria, and the analysis of air, water and ground (i.e., dirt, minerals, etc.) samples for similar substances. In manufacturing operations, materials can be tested to regulate or control the mixtures of substances, such as plastic, synthetics and petroleum, and the exhaust or byproducts of manufacturing operations can be analyzed to alert an operator of various different conditions, such as a malfunction.

Liquids can be identified for many different purposes, such as in airport security, stadium security or other security operations, or even authenticity, i.e., scanning a bottle of corked wine or sealed liquor to determine its identity, its condition or possibly even its age. Conversely, many substances and combinations of substances, such as certain liquids, can be tested to confirm whether they are what they claim to be. For example, when an airport traveler claims a clear liquid to be water, the liquid can be tested to determine whether it is water, and if it is not, the liquid and/or the traveler could be held for further investigation. Likewise, the authenticity of many other objects, such as money, bonds, antiques, documents, etc., can also be verified.

Referring now to FIG. 1, the present invention and its many applications will be described in greater detail. FIG. 1 is a block diagram illustrating the transmission, reception and analysis systems of the present invention. The CPU 10, I/O 12 and memory 14 can be configured as stand alone components when utilized in some applications or incorporated into a larger computer system 16 for use in other applications. For example, some scanning applications may require the present invention to be contained within a small, handheld, battery-powered unit that performs a limited application and only requires minimal processing, memory and data handling capabilities (See FIG. 6 for an example of such a device), while other applications may enable computer 16, incorporating the CPU 10, I/O 12 and memory 14, to be located away from the sample, thereby making many more applications possible.

Either the CPU 10 or the computer 16 is further connected to a transmitter 18 and a receiver 20, either directly as shown in FIG. 1 or through the I/O 12. The transmitter 18 is preferably capable of generating electromagnetic radiation across a broad spectrum. While many applications, and currently the best mode of the present invention, only require a frequency sweep between 1 MHz to 20 GHz, additional information about a sample and its characteristics can be achieved utilizing frequency sweeps in ranges from as low as 9 kHz, or lower, and as high as 810 THz, or even higher.

When the frequencies for a particular sweep enter the visible, infrared or other portions of the spectrum, different or additional transmission nodes and other equipment, as described further below, would be required in order to transmit such signals. Naturally, the receiver 20 must also be capable of operating in the same frequency ranges as the transmitter 18.

The type and arrangement of the nodes would also be impacted by the object being scanned. For example, while it might be possible to utilize an infrared transmitter and receiver placed on either side of a liquid or gaseous object, a more solid object might block the transmitted infrared signal from being detected by the receiver node. In such a case, it might be necessary to have the transmission node also operate as the receiver node, or to place the transmission node and the receiver node on the same side of the object, such that a deflected signal could be detected. Alternatively, a lower harmonic of the visible light signal could be utilized in place of the visible light signal. For example, if it were known that an element or characteristic of a gas or liquid could be detected using a visible light signal, that same element or characteristic should be detectable at a lower harmonic of the visible light signal, even though the distinguishing features of the element or characteristic would have a substantially lower magnitude and might be difficult to perceive in the lower harmonic signal.

As illustrated in FIG. 1, one or more transmission nodes 22 are connected to the transmitter 18 and used to transmit the electromagnetic radiation and one or more receiver nodes 24 are connected to the receiver to receive the electromagnetic radiation once it has been transmitted through or reflected by the sample. For the best mode of the invention, antenna components can be utilized for both the transmission node and receiver node, but at higher frequency levels, non-antenna transmit/receive components may be required.

Figure 2:
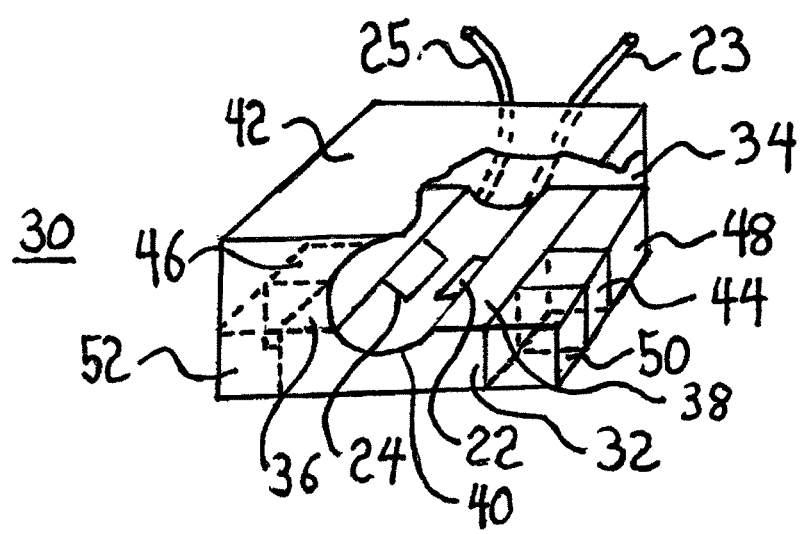
FIG. 2 is a partially cut-away, perspective view with hidden lines of the sample scanning apparatus of the preferred embodiment of the present invention.

One possible configuration of the transmission nodes 22 and the receiver nodes 24 is illustrated in FIG. 2, which provides a partially cut-away perspective view, with hidden lines, of a sample scanning apparatus 30 in conformity with the present invention. The sample module and scanning module or apparatus illustrated in FIG. 2 is designed for scanning applications where the sample to be tested, such as a finger of a human, or similarly shaped object such as a test tube or sample container, is placed inside the scanning apparatus 30. The base or bed 32 of the scanning apparatus is shaped in such a way that a finger or object placed within the scanning apparatus 30 will be held in a consistent position. Additional guides or stops can be arranged inside the scanning apparatus to ensure constancy of placement of the sample. For example, as illustrated in FIG. 2, the back wall 34 of the scanning apparatus 30 acts as a stop for the finger or object placed inside. The bed 32 is comprised of a left arm 36 and a right arm 38 with an angled or rounded central guide wall 40 formed there between. The rounded shape of the guide wall 40, in this particular application, helps to further insure consistent placement of an inserted finger or similarly rounded object.

The bed 32 is formed from a material that has a lower dielectric constant $D_k$ (as close to 1 as possible), such as Rexolite® 1422 (trademark of C-Lec Plastics Inc.). Rexolite is also presently preferred because its change in $D_k$ is negligible with temperature fluctuations. Although Rexolite is presently preferred, other materials could also be utilized and even some materials with higher dielectric constants or other properties not present in Rexolite could enhance some applications. Rexolite 1422 is a thermoset, rigid and translucent plastic with a dielectric constant of 2.53 (up to 500 GHZ) and an extremely low dissipation factor. The performance characteristics of the Rexolite 1422 bed 32 enables the transmission node 22 and the receive node 24 to be placed or embedded directly in the bed 32. The nodes 22 and 24 are spaced apart so as to enable a finger or object to be placed between the two nodes, such that any signal transmitted from the transmission node 22 would go through the finger or object to reach the receiver node 24. Highly shielded transmission lead 23 connects the transmission node 22 to the transmitter 18 and highly shielded receiver lead 25 connects the receiver node 24 to the receiver 20.

The shape and arrangement of the nodes 22 and 24 are application specific. As illustrated in FIG. 2, the arrangement of the nodes 22 and 24 and the other components of the scanning apparatus 30 are ideally suited for biometric testing, glucose level testing and similar types of applications, and represent the best mode for such types of applications. This same arrangement can be utilized to identify an unknown fluid contained within a test tube or sample container.

Other applications, however, might require different types of nodes 22 and 24, as well as other equipment, which might need to be arranged differently, to achieve the best results. For example, at high frequencies, such as 810 THz, many changes would be required of the scanning equipment, not just the nodes. For example, in the scanning device illustrated in FIG. 2, the transmission lead 23 and the receiver lead 25 presently utilize 50 ohm cables to carry power to the nodes. The reactive impedance from the nodes to the ground plane of the scanning apparatus 30 (not shown) through the base 32 has been minimized to about 50 ohms at 12 GHz. This impedance is determined by the capacitance of area and spacing of the nodes to the ground plane and the dielectric constant of the Rexolite base 32. Since reactive impedance varies as 1/frequency, at higher frequencies, very little power could be transmitted through such leads. Hence, at higher frequencies, very different equipment will be required to make the scanner operate effectively.

Figure 3:
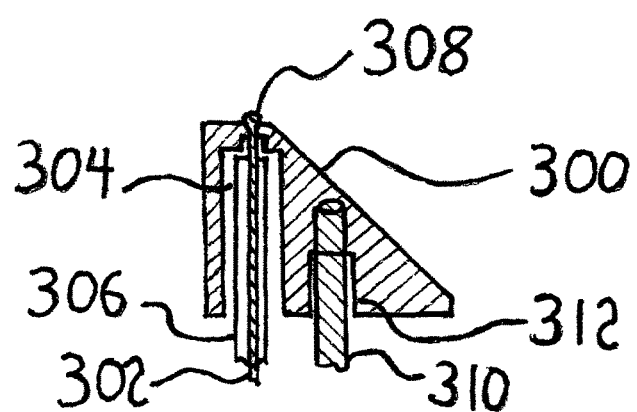
FIG. 3 is a cross-sectional view of either a transmission node or a receiver node of the preferred embodiment of the present invention.

The shape, orientation and material composition of the nodes can also improve the performance characteristics of the scanning apparatus 30. The present best mode shape and material composition of either of the nodes 22 and 24 is further illustrated in FIG. 3, which is a partially broken, cross-sectional view of either a transmission node or a receiver node of the preferred embodiment of the present invention. As shown in FIG. 3, the node is comprised of a metal base 300, preferable formed from solid brass with gold plating, although other non-reactive or low reactive metals or alloys could be utilized for the plating. The antenna 302 for the node is inserted into the base 300 through an opening 304 formed in the base 300. A Teflon (trademark of E.I. du Pont de Nemours and Company) sleeve 306, or a sleeve formed from other similar substances, fits around the antenna 302 until the antenna 302 enters a narrowed or tapered portion of the opening 304 near the top of the base 300.

To secure the antenna 302 to the base 300 and to provide an electrical connection between the antenna and the base 300, the top 308 of the antenna 302 is prick punched and affixed with a silver epoxy, although many other manners of securing and connecting the antenna 302 could be utilized. To affix or secure the base 300 to the bed 32, a Rexolite 1422 screw or post 310 is inserted into a second opening 312 formed in the base 300, which screw or post 310 is in turn affixed or secured to the base 32.

The orientation and location of the nodes 22 and 24, relative to one another and/or to a finger or object to be analyzed, can also affect the performance of the scanning device. As illustrated in FIG. 2, nodes 22 and 24 are preferably arranged and oriented within the bed 32 so as to enable the majority of most human index fingers to rest within the bed while making contact with both nodes 22 and 24. Likewise, an object to be analyzed could be shaped or placed within a container, such as a specially shaped container formed from a material such as Rexolite 1422 that would enable the object to rest within the bed 32 in contact (perhaps through the container) with both nodes 22 and 24. In some applications, contact between the finger or object to be analyzed and both nodes 22 and 24 is not necessary to enable detection of an adequate signal at the receiver node 24, but in other applications such contact can make a significant signal quality difference.

Although FIG. 2 illustrates the presently preferred embodiment of the present invention, with a single transmission node 22 and a single receiver node 24, which enable the creation of spectral data sets for development of composite spectrograms for analysis by the CPU 10, additional nodes can be utilized to create additional spectral data sets for additional composite spectrogram analysis. For each N number of transmission nodes 22 and M number of receiver nodes 24, a total of N×M spectral data sets become possible. The nodes 22 and 24 can also be arranged in arrays of two or more nodes to create further spectral data sets for composite spectrogram analysis.

As further illustrated in FIG. 2, the bed 32 including the nodes 22 and 24 are enclosed within a closed-top housing 42 that provides structural stability for the scanning apparatus 30, provides a clear opening for insertion of the finger or object to be tested, and which provides electrical shielding. The housing 42 could also be open-top, either partially open around the area in which a finger or object to be tested would be placed, or completely open on the top.

A housing 42 composed of a shielding material and providing somewhat less than 360 degree coverage, as illustrated in FIG. 2, would allow for simple insertion of the finger or object, would reduce electrical noise, and would reduce environmental interactions with any magnetic field generated within the housing, as further described below. The housing 42 would also include a base portion (not shown in FIG. 2) below the bed 32, magnets 44 and 46, and blocks 48, 50 and 52, to complete the housing enclosure.

The housing 42 could be formed of Rexolite 1422 or other materials, such as aluminum or copper. Alternatively, if the housing is to be used to also provide magnetic shielding, the housing 42 could be made somewhat larger to provide a sufficient gap or spacing from the magnets 44 and 46, at least 0.3 inches, and be fabricated from soft iron, mu-metal (a nickel-iron alloy (75% nickel, 15% iron, plus copper and molybdenum) that has a very high magnetic permeability) or other similar metal of sufficient thickness to prevent saturation of the metal. The housing 42 could also be fabricated to include RF shielding, such as an attunement shield that tunes in or out certain frequencies to deaden or enhance information in the composite spectrograms.

The scanning apparatus 30, as illustrated in FIG. 2, also includes magnets 44 and 46 positioned on the outside of arms 36 and 38 that form a magnetic field around the nodes 22 and 24 and the object to be tested. For some applications of the scanning apparatus 30, the magnetic field created by the magnets 44 and 46 is completely irrelevant and the magnets should not be utilized. In other applications, the magnetic field enhances the analysis of the composite spectrograms, but is not required. In still other applications, such as glucose testing, the magnetic field is required to generate a usable composite spectrogram.

When a magnetic field is desirable, high-gauss permanent bar magnets, made of a Neodymium compound ($Nd_2Fe_{14}B$), cylindrically shaped of dimensions 1.25 inches long by ⅝ inches in diameter of 50 MGOe (Mega Gauss Oersted) are presently preferred, although other magnets of different compositions, shapes, and strengths and even nonpermanent magnets (created using electromagnetism) could be utilized. The shape, position, strength and number of magnets 44 and 46 utilized is important with respect to configuring the position of the magnetic field relative to the transmission node 22 and receiver node 24 and the sample to be tested, and the intensity of that magnetic field. FIG. 2 illustrates a preferred embodiment of the present invention with magnets 44 and 46 positioned on the outsides of arms 36 and 38 and held in place on the sides of the magnets 44 and 46 by Rexolite 1422 blocks, such as block 48 and blocks 50 and 52 illustrated with hidden lines. A block corresponding to block 48 would be positioned next to magnet 46, but is not visible in FIG. 2 due to the presence of the housing 42.

The position of the magnets 44 and 46 as illustrated in FIG. 2, with the north pole of magnet 44 and the south pole of magnet 46 facing the front of the scanning apparatus 30 and the south pole of magnet 44 and the north pole of magnet 46 facing the rear of the scanning apparatus 30, creates a magnetic field that surrounds the nodes 22 and 24 and any portion of the sample to be tested that is positioned between the nodes. As configured, the magnetic field near the rear of the nodes 22 and 24 is near zero and drops to zero about 1 mm from the back of the nodes towards the rear of the scanning apparatus 30. The magnetic field strength near the front of the nodes 22 and 24, midway between the nodes and in the place through the centerline of the two bar magnets 44 and 46, is on the order of 300 gauss. This particular magnet/node configuration is the preferred embodiment for the scanning applications ideally suited for the scanning device 30, as noted above. Other applications and other scanning apparatuses, however, might achieve better results with different configurations of magnets and nodes, such as illustrated in FIGS. 4a and 4b.

Figure 4A:
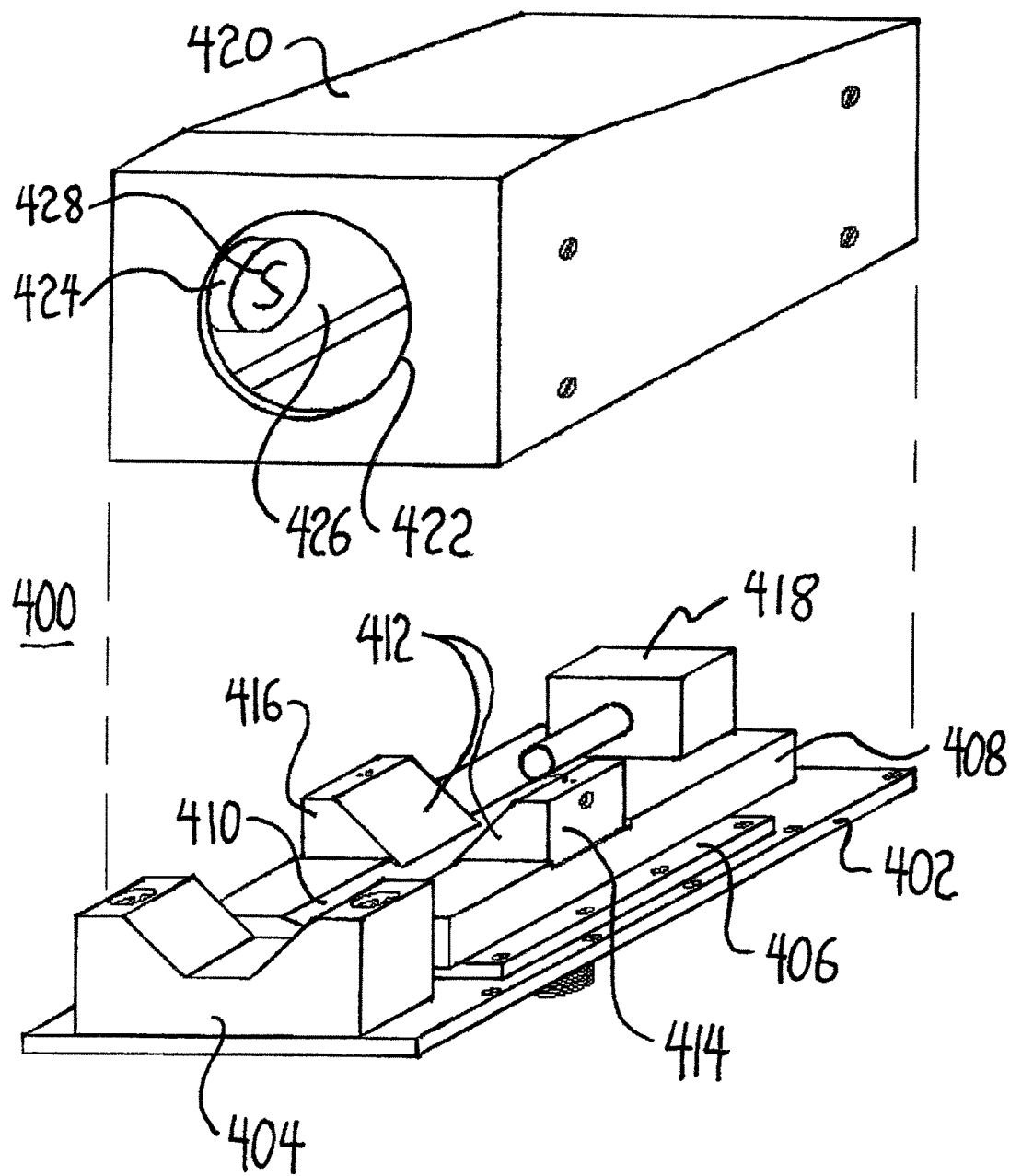
FIG. 4a is a partially exploded, perspective view of a first alternative embodiment of the present invention including one pair of nodes and two pairs of magnets.

FIG. 4a is a partially exploded, perspective view of an alternative embodiment of the scanning apparatus illustrated in FIG. 2. The scanning apparatus 400 of FIG. 4a is comprised of one set of nodes and two sets of magnets. A base 402 supports a finger guide 404, made of Rexolite or a similar material, and a riser plate 406. Riser plate 406, which is preferably formed of a brass material and which operates as the RF ground return, supports a bed 408 with a central trough 410 and a first node set 412 comprised of a transmission node 414 and a receiver node 416. The bed 408 also supports a stop 418, which operates in conjunction with the shape of the finger guide 404, the trough 410 of the bed 408, and the first node set 412 to position a finger, sample or object in the correct position and orientation within the scanning apparatus 400.

A housing 420 fits over the top of the base 402 to complete the enclosure and to provide a magnetic field through the nodes and sample in addition to RF and/or magnetic shielding, when needed. Housing 420 also forms an opening 422 through which a finger, sample or object could be inserted. The housing 420 also supports two sets of magnets that are affixed to the opposite inner sides of the housing. Only magnet 424, of a first set of magnets, is illustrated in FIG. 4a, affixed to the left inside wall 426 of the housing 420, with the south pole 428 of magnet 424 facing the inside of the scanning apparatus 400. Another magnet, with its north pole facing inward would be positioned on the right inside wall of the housing 420 opposite magnet 424. Likewise, a second set of magnets, not shown, would be similarly affixed to the inside walls of the rear of housing 420, facing in opposite directions and with their poles reversed in comparison to the first set, i.e., the magnet on the same side of the housing 420 as magnet 424 would have its north pole facing the inside of the scanning apparatus 400.

Figure 4B:
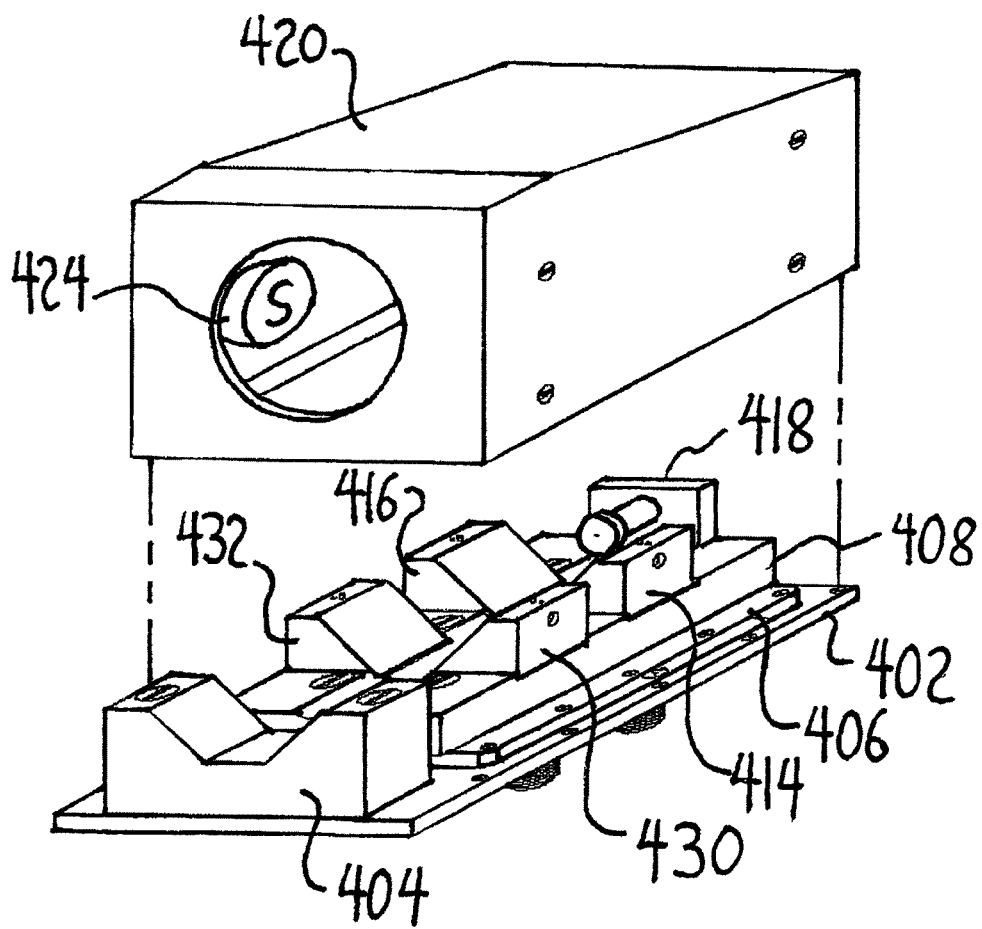
FIG. 4b is a partially exploded, perspective view of a second alternative embodiment of the present invention including two pairs of nodes and two pairs of magnets.

FIG. 4b is almost identical to FIG. 4a, but includes a second node set comprised of a second transmission node 430 and a second receiver node 432. With respect to both FIGS. 4a and 4b, the base 402 is presently 2.2 inches wide, 3.2 inches deep, and 0.10 inch thick. The housing 420 is 1.67 inches tall at the front. All of the remaining parts of the scanning apparatus 400 are scaled accordingly. The scanning apparatus 30 of FIG. 2 is similarly sized. Of course, other sizes and configurations are possible and might be preferred for different scanning operations. Accordingly, the present invention anticipates many other possible sizes and configurations and is not limited by the sizes and configurations illustrated herein.

While scanning apparatus 400 could be used for applications the same as or similar to scanning apparatus 30, its arrangement of one or two node sets and magnet sets would create different composite spectrograms and would therefore create different useful applications. For example, scanning apparatus 30 is particularly well suited for glucose and blood scanning applications, and while apparatus 30 could be used for biometric identification, it is preferable to utilize a smaller-sized device, such as apparatus 400 for biometric identification. It has been found that even minor changes in the dimensions, angles, materials, shapes and other features of the magnets, nodes and other components of the scanning apparatus, as well as the position of the sample to be tested, the frequencies used by the scanning apparatus, the strength of magnets if utilized, whether the sample is in contact with the nodes, the volume of the sample, and many other factors can have a small to significant impact on the performance of the scanning apparatus and the analyzer.

It is therefore necessary to perform a tuning operation with each new configuration of the scanning apparatus and its components, the electronics and the analyzer in order to get the best results, or in some cases any results. At the present time, a certain amount of trial and error is required to tune a scanning apparatus for a particular application. For example, in glucose level scanning, the subject's finger should be in contact with both nodes and a magnetic field should be used. It may be possible, however, to find a particular arrangement or configuration of the components within the scanning apparatus that will remove the need to have the subject's finger in contact with the nodes, or to use the magnetic field.

In other tests, neither of these requirements may be necessary. For example, in some manufacturing applications where a fluid or gas is being tested for its composition, it may be preferable to insulate the nodes from the fluid or gas so that there would be no contact between the matter being tested and the nodes. In most applications, the magnetic field is not required, but the presence of the magnetic field may substantially enhance the performance of the scanning apparatus for some applications.

For many of the applications of the scanning apparatuses 30 and 400, the method of sampling would be similar, but many alternative embodiments would be possible for alternative applications. In a finger scanning application, direct sample scanning application (where the sample is appropriate to place directly into the scanning apparatus), or where the sample can be placed inside a container that can then be placed inside the scanning apparatus, it is preferable to place the finger, sample or container in direct contact with the transmission node and the receiver node. Such direct contact helps to improve or enhance the quality of the signal received by the receiver node after passing through the sample, such as through reduction in the amount of other signals (noise) that can be picked up by the receiver node at the same time and the amount of power loss (reduction in amplitude) in the received signal.

Once the sample is in position in the scanning apparatus, a series of electromagnetic radiation signals covering a range or sweep of frequencies is transmitted from the transmission node(s) to the sample and to the receiver node(s). The amplitude of these signals can be the same or varied as different applications may require. This series of signals may be comprised of short signal bursts at each of a large number of distinct frequencies with small or large gaps between each frequency selected. When scanning for glucose or blood sugar levels using the scanning apparatus 30, the preferred frequency sweep is between 100 MHz and 3 GHz, but frequency sweeps from 10 MHz to 2.7 GHz and 100 MHz to 12 GHz have also been used successfully. For biometric identification scanning, a sweep of 10 MHz to 12 GHz is presently preferred due to economics and physical configurations. Much higher frequencies would be preferred, but utilizing higher frequencies requires a different physical configuration of the scanning apparatuses 30 and 400 and requires significantly more computational power to process the resulting spectral data sets and composite spectrograms.

For many applications, the transmitter 18 could be a commercially available signal generator, such as the Agilent Technologies' Agilent E8257D PSG Analog Signal Generator, which is capable (when properly accessorized) of synthesizing signals with high output power (at least 20 milliwatts, based on a constant peak to peak RF voltage of one volt and impedance of 50 ohm) and low phase noise in ranges between 250 kHz and 325 GHz. Likewise, the receiver 20 could be a commercially available spectrum analyzer, such as the Agilent Technologies' Agilent ESA E4407B Spectrum Analyzer, which is capable (when properly accessorized) of receiving and analyzing signals in ranges between 9 kHz and 325 GHz. More specialized equipment may be required to transmit and receive signals at lower or higher frequencies. Likewise, specific electronic circuitry capable of performing the same types of functions, in place of the signal generator and spectrum analyzer, could be developed for use in the present invention.

Spectrum generators, analyzers and similar electronic circuitry are commonly used to generate signals and to examine the resulting waveforms. Many such devices allow the user to select the number of sampling points at which signals will be transmitted within a particular frequency range, thereby determining the selected frequencies as well as the gaps between those frequencies. For example, in a frequency range from 100 MHz to 12 GHz, 3201 sampling points are selected (based on the capabilities of the equipment noted above and the compute time required to process that many sample points), although a different number of points could readily be utilized with the same or different equipment and greater computational power. In specially designed circuitry, it would be possible to specify the exact frequencies for each sampling point, which might give a user even further flexibility in terms of scanning a sample at the frequencies most likely to generate the most useful information.

The presence of the sample, and in particular the composition of the sample at the particular moments during scanning, modifies the amplitude of at least some of the signals transmitted through or reflected by the sample from the transmission node(s) to the receiver node(s). There are numerous possible explanations as to why the amplitudes of the signals are modified at different frequencies, but the explanations are not as important as the end result. In many cases, the amplitude is reduced, but in some cases, the amplitude is actually increased. It is possible that amplitude modification might result when electron spins are excited by the electromagnetic radiation, as well as the presence of a magnetic field, when utilized. But electron spin resonance is only believed to occur when a molecule has an unpaired electron, such as a free radical in an organic molecule or a transition metal ion in inorganic complexes, and since most stable molecules have a closed-shell configuration without a suitable unpaired electron, electron spin resonance cannot be the only basis for amplitude modification. Additional amplitude modification could therefore result from proton spins of radiated atomic nuclei.

It is also possible that additional amplitude modification could result when electromagnetic radiation is absorbed or emitted by molecules associated with a corresponding change in the rotational quantum number of the molecules, otherwise know as rotational spectroscopy or microwave spectroscopy. However, rotational spectroscopy is believed to only really be practical when molecules are in the gas phase where the rotational motion is quantized. In solids or liquids, the rotational motion is usually quenched due to collisions.

As previously noted, the possible physical explanations behind the amplitude modifications are not as important as the amplitude modifications themselves. These modifications have particular meaning with respect to certain characteristics of each sample that can be determined from careful analysis of the resulting composite spectrograms (as described below). This point is particularly important with respect to distinguishing the present invention from numerous prior art techniques in which a composite signal is examined, but usually only at one or two frequencies, to determine the presence of an analyte. These prior techniques do not look at a composite spectrogram, which represents an amassed congeries of data collected at many different frequencies, in order to perceive subtle quantitative relationships within that composite spectrogram or between compared composite spectrograms.

In all scanning apparatuses, even those with a single node, a single pair of nodes, or multiple transmission and receiver nodes, frequency sweeps could be further varied. For example, a first signal could be transmitted from a first transmission node and only detected by a directly, physically corresponding first receiver node, and then a second signal could be transmitted from a second transmission node and only detected by a second receiver node that directly, physically corresponds to the second transmission node, etc. Since all transmission nodes are also capable of receiving, it is also possible to transmit from one node and receive on all of the nodes, including the transmission node. Thus, it would be possible to transmit from a first node, receive on three other nodes and the first node, transmit on a second node and received on the first node, the second node, and two other nodes, etc.

Alternatively, the first signal could be transmitted from the first transmission node, but only detected by the second receiver node, while the second signal is transmitted from the second transmission node, but only detected by the first receiver node, etc. Additional arrangements of nodes and magnets (if used), including arrays of nodes, could create countless additional variations, including the transmission from a first transmission node and near simultaneous detection by multiple different receiver nodes.

Likewise, although a consistent orientation and position of the sample to be tested has so far been discussed, the position and orientation of the sample could also be varied from test to test or within a single test. For example, a sample could be placed in the scanning apparatus in a first position, then scanning would be performed, then the sample would be rotated by some number of degrees (45°, 60°, 90°, 180°, etc.), and scanning would be performed again. This would result in multiple composite spectrograms that could be used to improve performance or the reliability of identity scanning, etc.

The position of the sample in the scanning apparatus could be further changed by varying the extent of insertion into the scanning apparatus for each test. For example, a finger could be inserted at a first position, where maybe just the finger tip is in contact with a first set of nodes, and then inserted further to a second position, where the first knuckle is in contact with the first set of nodes, etc. In biometric identity scanning applications, position and orientation variations, as well as scanning variations, could be used to increase the distinctive information that is collected regarding the subject's bone structure or other distinguishing features. Additional samples, such as a second finger, could also be used to enhance scanning.

Figure 5:
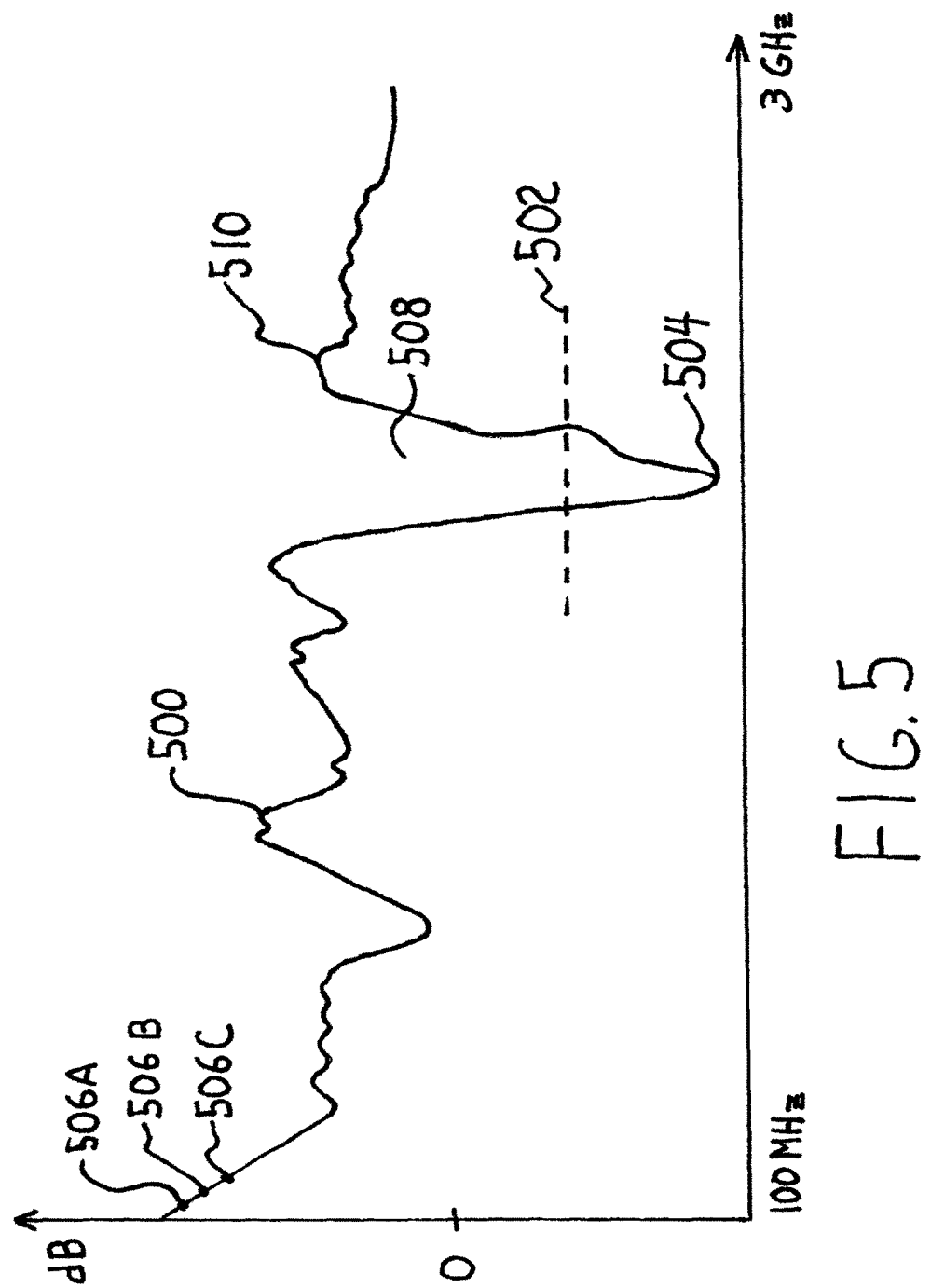
FIG. 5 is an illustration of a composite spectrogram display for glucose scanning in accordance with a further alternative embodiment of the present invention.

Details of the analysis of a scanning application is described with reference to FIG. 5, which illustrates a composite spectrogram signal for glucose level testing in accordance with a preferred embodiment of the present invention. FIG. 5 depicts a composite spectrogram that is utilized to make a determination about a subject's glucose level, which can be made without prior information about the subject (other than the cross-sectional area of the subject's finger, which is necessary to account for blood volume, as noted below). In other words, no subject specific calibration is required, the subject need not perform pin prick tests or use other glucose testing technologies as a gauge to determine the reliability of a test using the present invention, and no pattern matching with prior tests of the subject are required. Naturally, combining such a determination with calibration and pattern matching could improve the accuracy of the analysis and enhance any necessary interpolation between known patterns.

As disclosed in the '048 patent, the contents of which is incorporated by reference herein, it is known that a change in the magnitude of an RF signal transmitted through a finger occurs at about 2.48 GHz and that this change in magnitude correlates to the concentration of glucose or blood sugar in the finger. However, the '048 patent relied upon basic pattern matching at the specified frequency with previous tests to make a determination about a current test and a subject's current glucose level.

The present invention utilizes real-time pattern recognition analysis to make determinations about the glucose levels of the subject represented by the composite signal. The pattern recognition analysis is based on additional information found at other frequencies in the composite signal (other than about 2.48 GHz), together with additional data about the subject to be tested. The scanning apparatus of the present invention enables certain characteristic patterns to be detected that are common to subjects with high, normal and low glucose levels. Additional patterns also indicate when a subject is exerting excessive pressure on their finger or when their finger is not properly placed within the scanning apparatus. Still further patterns indicate when a subject has moved their finger during scanning or when a subject's finger is not oriented in the optimal position. Finally, the size of a subject's finger can result in significant variations in the composite signal, which variations can be diminished by accounting for the greater blood volume that exists in large fingers and the lesser blood volume that exists in small fingers, such as through measurement of the finger to be tested at a common point.

As a result, the analysis of the composite spectrogram signal of the present invention, performed by software or specialized hardware within the computer 16, takes advantage of real-time software pattern recognition analysis in order to perform accurate analysis of a just-in-time captured composite spectrogram signal. This method of analysis of the composite signal enables more complex determinations to be made about the information represented by the composite signal than would be possible using computerized pattern matching or human operators. More importantly, this method of analysis enables rapid determinations about a subject's glucose level without prior knowledge of that subject (other than finger size). Hence, a scanning device incorporating this technology could be placed in homes, businesses and common areas of stores, much like current blood pressure testing devices, and enable anyone utilizing the device to obtain an accurate measure of their current glucose level.

Other devices, such as portable scanning devices that do not require pin pricks, which could be put in a pocket or purse, would make many other types of applications possible. For example, since the quantity of glucose or blood sugar in a person's body at a given point in time is representative of the calories they have consumed and utilized as a result of exercise or simply living, their blood sugar level correlates well to their weight or performance management. If their blood sugar levels are higher than a normalized level, they may be in a position to gain weight, while if their blood sugar levels are lower than a normalized level, they may be in a position to lose weight. While this correlation is well known and incorporated into a number of weight management plans, prior art blood sugar testing devices have not made it practical to test someone's blood sugar levels multiple times a day to help manage their caloric intake and utilization. The present invention changes this situation, however, by enabling a user to carefully test and manage their caloric intact and utilization many times during the course of a day, thereby enabling use by anyone desiring to control their weight, including athletes, dieters, etc.

Likewise, an athlete's performance could be optimized through use of such a device by carefully monitoring blood sugar levels to make sure the athlete had the optimum amount of fuel for energy in their body at a needed time.

By coupling the blood scanning features of the present invention to a computer equipped with additional weight management software, a user could track their weight gain or loss over a period of time, but without being relegated to making rough guesses about calories consumed, through food and drink, and utilized, through normal body functions and exercises performed. Performance management software could play a similar cooperative role. Alternatively, the present invention could be coupled with a calorie counting type of diet, so as to prevent the user from straying from reality (i.e., "that donut was only 50 calories" or "I only had a half portion"). Certain safety features could also be incorporated if a user was consuming too few calories over a period of time or exercising too much, such as by disabling the scanning device or sending a message to a central office so as to enable a person to check on the user.

With reference now to FIG. 5, an example of just-in-time composite signal analysis, in conformance with a preferred embodiment of the present invention, is provided. The composite signal illustrated in FIG. 5 is representative of the type of signal generated during a glucose level test. The graph of the composite spectrogram signal 500 in FIG. 5 represents frequency, in Hertz (Hz), along the horizontal axis and differential amplitude, in decibels (dB) along the vertical axis.

Figure 7:
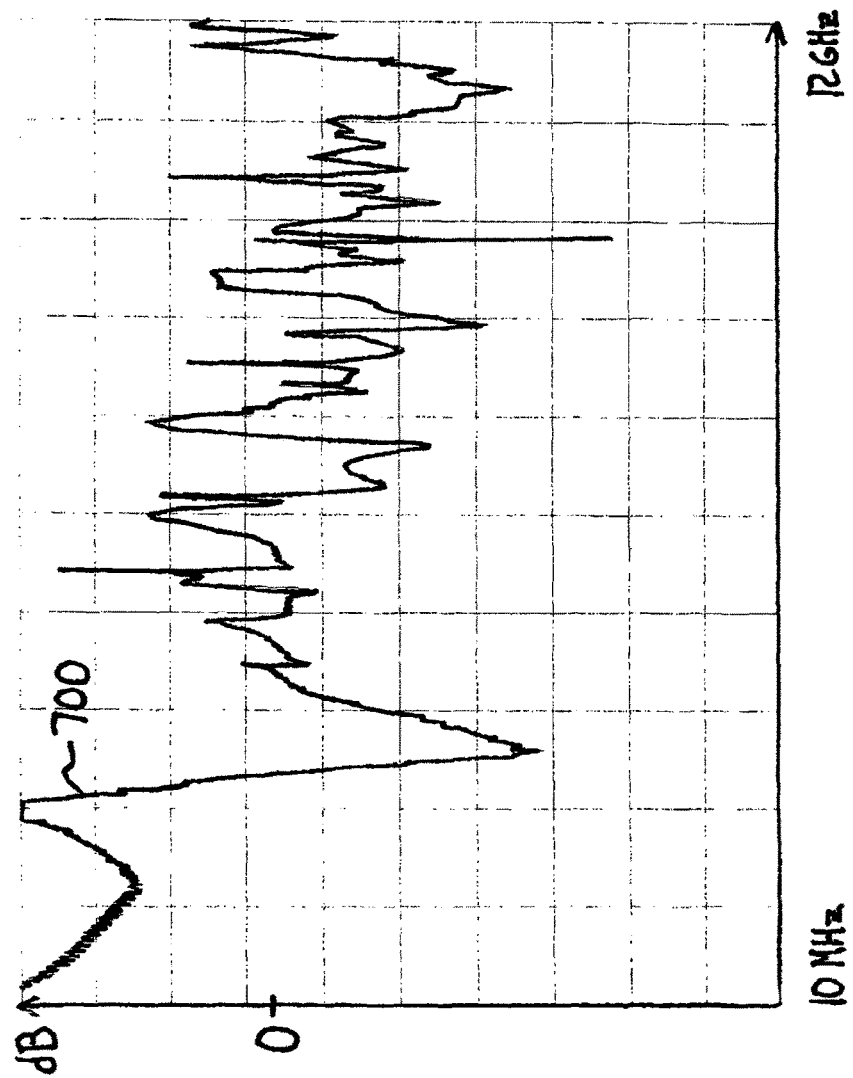
FIG. 7 is an illustration of a real-time composite spectrogram for biometric identification in accordance with a preferred embodiment of the present invention.
Figure 8:
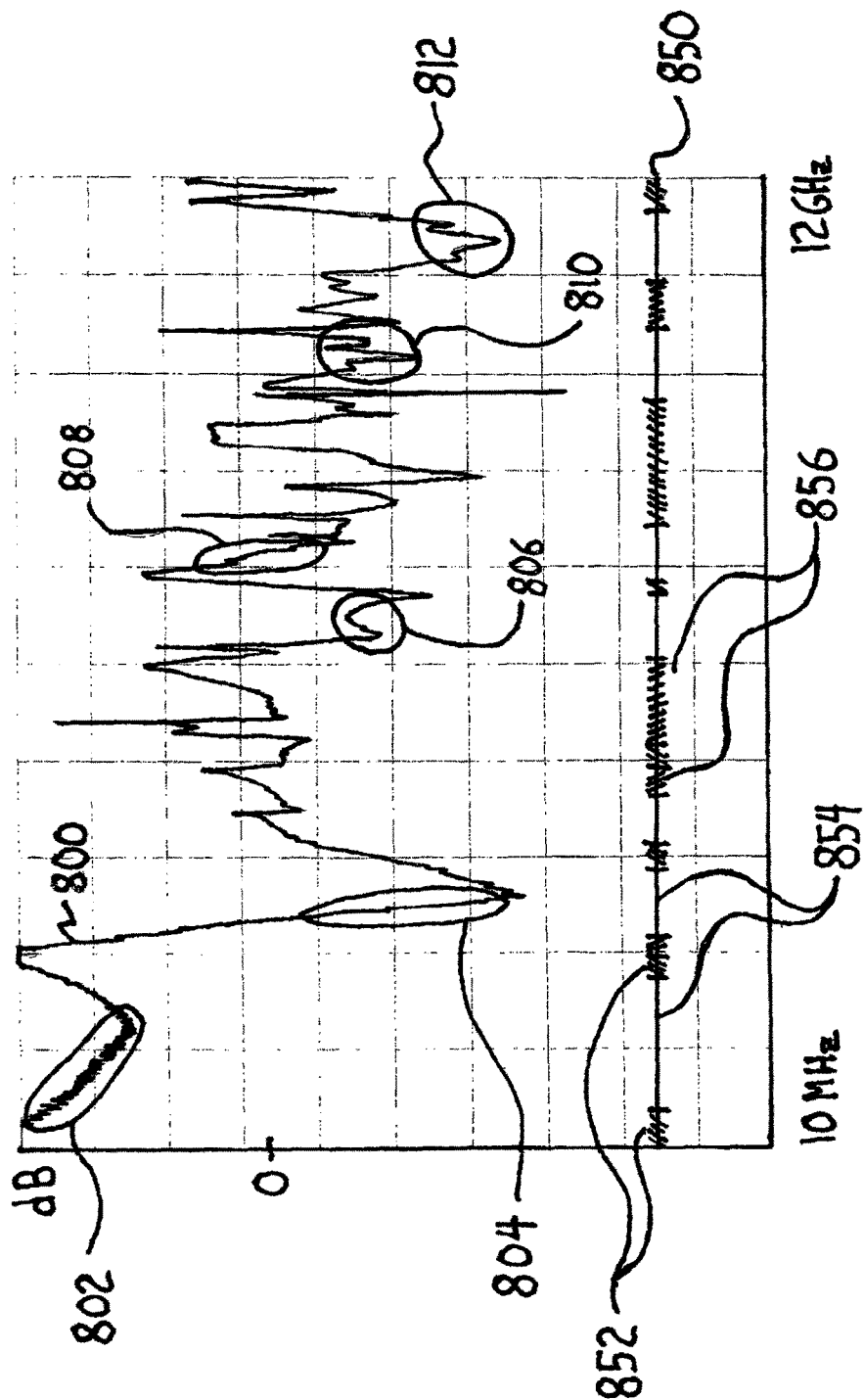
FIG. 8 is an illustration of a stored spectrogram for comparison to the real-time spectrogram of FIG. 7, and further illustrating the areas of difference and the regions of relevance between the two spectrograms.

Although the power or magnitude of the resulting composite signal could be represented in a number of different ways, decibels are preferred for representing changes in the amplitude of the composite signals because decibels effectively represent ratios, which can be particularly useful when comparing amplitude levels to a baseline, as further described below. Also, the term "differential amplitude" is used to refer to the normalized amplitude signals that are generated by performing a scan first without a sample, performing a scan with the sample to be tested, and then subtracting the amplitude versus frequency results of the first scan from the results of the second scan. As illustrated in FIGS. 5, 7 and 8, the zero differential point is shown by the "0" at the approximate midpoint of the vertical axis in each graph. While it would be possible to perform a single scan of a sample without normalizing the signal(s), the resulting signal(s) would likely be noisy and less reliable so it is preferable to use normalization.

There are four pattern components to the composite signal 500, and a fifth factor, a measure of the blood volume of the subject's finger, which are used to determine the subject's glucose level from the composite signal 500. When scanning for blood glucose levels, it is very important to determine at least a rough determination of the blood volume of the subject's finger, i.e., the size of the finger, at the point of measurement because smaller than normal and larger than normal fingers can skew the results if the resulting blood volume (less for small fingers and more for large fingers) is not taken into consideration.

Hence, the cross-sectional area of the finger at the approximate point of contact with the nodes is determined. This determination can be made in any of a wide variety of fashions, such as measuring the subject's finger with a piece of measuring tape, matching the subject's finger to a model of known size, or even including an automated finger measuring device inside the scanning apparatus that applies a small cuff or similar band around the finger to determine its size prior to scanning. The effect of this measurement on the glucose level determination will be discussed more fully below.

The dashed baseline 502 in FIG. 5 represents a decibel level, at the approximate 2.5 GHz frequency, that highly correlates to normal glucose levels. While the baseline 502 cannot be reliably used as the sole basis for measuring glucose levels, in the absence of comparative pattern matching as disclosed in the '048 patent, it can be used in conjunction with four other components of the composite signal 500 to reliably determine glucose levels without pattern matching. When referring to each of these components below, a reference to a component being "high" or "low" is in comparison to a median point for that component, and a reference to a component being "positive" or "negative" is relative to the scale position of "0" on the decibel vertical scale.

It should also be noted that the composite signal illustrated in FIG. 5, including the peaks, valleys and other signal components, is based on the shape and strength of the magnetic field, the transmitting and receiving nodes, and numerous other factors, as previously discussed. The exemplary composite signals illustrated in FIGS. 5, 7 and 8 were created using a scanning device similar to that illustrated in FIG. 2. Changes in this device or the use of a differently configured device, such as illustrated in FIGS. 4a and 4b, might cause the peaks, valleys and other signal components to shift up or down in frequency or cause other changes that would have to be accounted for in analyzing the resulting composite signal.

The first pattern component is the lowest point 504 (or decibel level) of composite signal 500. This lowest point typically occurs, but does not always occur, at approximate 2.5 GHz. When the lowest point 504 is at the baseline 502, the glucose level of the subject is most likely normal. When the lowest point 504 is above the baseline 502, the glucose level of the subject is most likely high. The further away the lowest point 504 is from the baseline, in the positive direction, the higher that glucose level is likely to be. Likewise, when the lowest point 504 is below the baseline 502, the glucose level of the subject is most likely low. The further away the lowest point 504 is from the baseline, in the negative direction, the lower that glucose level is likely to be. The terms "most likely" and "likely" are utilized because as previously stated, the baseline 502 alone, or comparison of the lowest point 504 to the baseline 502, only provides a rough estimate of a subject's glucose level, but it cannot alone be reliably utilized to determine a subject's glucose level, which is where the other components come in to play.

Sampling points 506A, 506B and 506C, which are sampled at a low frequency (approx. 100 MHz), represent the sample variation pattern component. This component is important because a subject inserting their finger into the scanning apparatus may exert more or less pressure on their finger, or move their finger around, which can cause the composite signal 500 to move around as well, and causing all of the other components to change in some way. However, by sampling the composite signal 500 at each of the specified sampling points 506A, 506B and 506C, it is possible to remove many of the variations caused by finger movement or variation. For example, if the slopes of the lines formed between the three sampling points 506 are high, then the magnitude of the lowest point 504 is adjusted more toward 0 dB. If the slopes of the lines formed between the three sampling point 506A, 506 B and 506C are low, then the magnitude of the lowest point 504 is adjusted more negative.

The next pattern component is the trough 508 in the composite signal 500 formed by the lowest point 504. In its simplest form, the trough component 508 can just be a measure of the width of the trough at a point just above 0 dB, or the entire area of the trough can be calculated. When utilizing width, if the magnitude of the trough component 508 is high (or wider than the median), then the magnitude of lowest point 504 is adjusted more negative. When the magnitude of the trough component 508 is low (or narrower than the median), the magnitude of the lowest point 504 is adjusted more toward 0 dB. Area is utilized in the same way, with a larger area being used to adjust the lowest point 504 more negative, and a smaller area being used to adjust the lowest point 504 more toward 0 dB.

The last fine-tuning pattern component is a high frequency signal at a specified point 510 at the end of the trough 508. The fine-tuning component is used for just that, to fine-tune the accuracy of detecting the blood glucose level for about 80% of subjects. The fine-tuning component, however, should not always be used because in the remaining 20% of cases, the use of the fine-tuning component could actually lower the accuracy of the measured blood glucose levels of those subjects. Hence, it might be necessary to analyze signal 500 with and without the fine-tuning component to see if the results of the analysis improves with such use, and if it does not, then do not use it. When the fine-tuning component is used, if the magnitude of the specified point 510 is lower than the median, then the magnitude of the lowest point 504 is moved toward 0 dB. When the magnitude of the specified point 510 is higher, the magnitude of the lowest point 504 is moved more negative.

Composite spectrogram analysis utilizing different algorithms to detect quantitative relationships or to recognize patterns, similar in some ways to those techniques described above, could also be used to measure many other aspects of a subject's physical condition or composition, as well as many other characteristics of other types of samples. For example, composite spectrogram analysis could be used to measure or detect the presence of cholesterol (HDL and LDL as well), red and white blood cells, proteins (including antigens for determining blood type), hormones, steroids, lipids, C-reactive proteins, bacteria, yeast, viruses, pathogens, heavy metals, calcifications, and other biological markers, agents or substances. Once one or more components of a composite signal have been identified as corresponding to any substance that can be found in the blood, tissue or bone of a subject, the presence and levels of that substance can be detected and measured utilizing the present invention, without invading the subject's body, without having to compare that subject's current results with prior results, and in near real-time due to the speed of the computer aided analysis.

This would enable doctors and emergency medical technicians to perform on the site blood and tissue analysis without further traumatizing the subject and without endangering the doctors or technicians with potentially tainted blood. For example, being able to promptly determine if a patient had consumed alcohol, illegal drugs or even prescription drugs prior to or while transporting that patient to the hospital could prove life-saving in many situations. It would also enable doctors to perform more appropriate diagnosis and treatment of patients without all of the delay created by the current need for blood testing laboratories. It could also take the place of urine analysis testing or blood testing to test drivers, athletes, students, inmates, parolees, employees and countless others for the use of controlled substances, absorption levels of prescription drugs, alcohol and other foreign substances.

When a device in accordance with the present invention is utilized in a physical facility, the size, construction and operation of the device may be less critical than when utilized in a remote location, such as at the scene of an accident, the side of the road, or at multiple access locations throughout a building. The cost associated with installing bulky machinery at multiple different locations, or the impracticality of utilizing such machinery at a remote location, requires a different solution.

Figure 6:
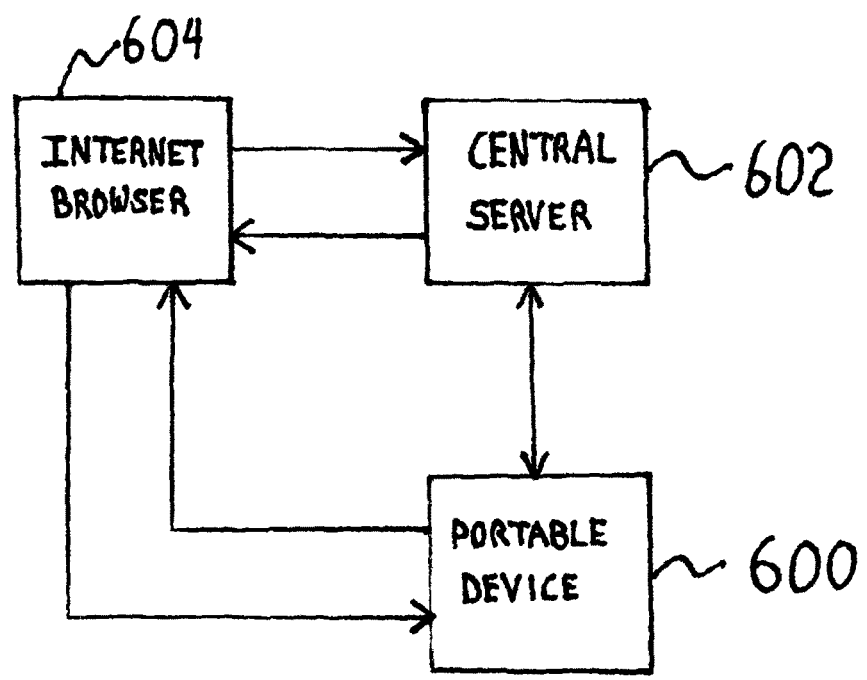
FIG. 6 is a block diagram illustrating a remote detection and analysis configuration in accordance with a preferred embodiment of the present invention.

One potential alternative solution is illustrated in FIG. 6, which illustrates a portable scanning device 600 that is capable of capturing raw data from a person or object to be tested at a remote location and wirelessly communicating that raw data to a central server 602. The raw data collected by device 600 could, in turn, be encoded utilizing digital rights management technology, or some similar type of encryption or data rights management technology, so as to further prevent a competitive device from being able to compatibly communicate with the central server 602. The server 602 would then process the raw data according to one or more proprietary analysis programs to produce a diagnostic result for the raw data and wirelessly communicate the diagnostic result back to the device 600. In some applications, the portable device 600 could be very simple and include a few predetermined scanning operations (selected through operation of a physical or electronic button on a touch screen), such as an alcohol test, a methamphetamine test, and one or two other tests, that could be selected by a law enforcement official in the field prior to collecting and communicating the raw data.

In other applications where the user of the remote device wanted a further range of tests, or so as to further reduce the cost of equipment at a remote location or a physical facility and to maintain control over the analysis program, the portable device 600 could be combined with an Internet browser 604 so as to enable the user to operate Internet-enabled applications and to perform other functions. For example, a personal query could be communicated from Internet browser 604 to central server 602 requesting the performance of one of a large number of different tests. The central server 602 would then communicate with the portable device 600 to request and collect the necessary raw data, which would be communicated back to the central server 602. After processing the raw data, the central server 602 would then communicate the diagnostic results, as well as other data, such as tabulated charts and histories, medical opinions, interpretations and other data, back to the browser 604 for the user. The portable device 600 could be configured to identify itself to the central server 602 for each test to be run or for each data package to be sent, so that the user of the portable device 600 could be charged accordingly, such as on a per test/per download basis, on account, etc. Other forms of identification and payment arrangements could also be possible depending on how much intelligence and how many user interface controls are built into the portable device 600.

While many characteristics of a sample can be detected and measured only using just-in-time analysis based on the recognition of pattern components, to improve the accuracy of the results of some tests, it is desirable to also use some form of pattern matching. For example, biometric identification applications naturally require a composite spectrogram signal representing a currently tested person to be compared to a database of previously tested persons to positively identify the person being tested or to reject them. However, it is neither necessary, nor desirable, to rely on the pattern matching test alone, especially when recognized pattern components can be used to improve the overall analysis.

FIG. 7 is a real-time spectrogram (R) 700 representing a person (P) who was just scanned or tested in accordance with the present invention. As with FIG. 5, the vertical scale represents decibels and the horizontal scale represents frequency, only unlike FIG. 5, in FIG. 7 the frequency scale ranges from 10 MHz to 12 GHz. The composition spectrogram (signal) illustrated in FIG. 7 includes a number of prominent peaks and valleys, the combined position and shape of which, after processing, are unique to every person.

While changes in a subject's general physical condition, recent dietary consumption, or other factors might alter their composite spectrogram from day to day, week to week, or month to month, possibly causing one person's signal to approximate another person's signal, many of these variances can be filtered out and otherwise accounted for to help reveal each person's unique spectrogram signal shape. For example, it has been observed that some regions of the composite spectrogram change much, while other areas change little, so from scan to scan the raw data can be inconsistent. By applying a filter to a composite spectrogram as part of a recognition algorithm, it is possible to filter out some of the courser variations in the raw data, while minor variations can be accounted for through quantitative analysis of the raw data, thereby enabling the recognition algorithm to focus on the areas of the composite spectrogram that represent unique characteristics of an individual.

FIG. 8 is a stored spectrogram (S) 800 representing the same person P in FIG. 7, but which was previously scanned from person P and stored in memory 14 for comparative purposes by CPU 10. If S 800 is known to represent person P, but R 700 is unknown, then it would make sense to compare R 700 to S 800 in order to determine if R 700 also represents person P. However, while a visual or electronic comparison between the two spectrograms 700 and 800 would illustrate some differences, not all of these differences are important because it is known that some components of the spectrograms change frequently, even for the same person, and are not considered reliable identifiers, while other small changes in a signal component are infrequent and might have great significance from an identifying perspective. For example, it is presently preferred to perform the following six comparisons to identify changes that may be of significance: $\alpha\emptyset$, $\alpha1$, $\alpha2$, $\beta\emptyset$, $\beta1$ and $\beta2$, where $\alpha$ represents a change in spectrograms of a single person versus herself/himself, where $\beta$ represents a change in spectrograms of a single person versus a different person, where $\emptyset$ represents a small change, where 1 represents an infrequent change, and where 2 represents no change.

With respect to FIGS. 7 and 8, the primary components or areas of difference between R 700 and S 800 are illustrated on FIG. 8 as the circled areas 802, 804, 806, 808, 810 and 812, although other slight differences might exist between the two signals in other areas. These differences can be quantified using a number of different techniques, such as a filtering algorithm or even the least squares or the sum of the squared error technique, which is a mathematical optimization technique that attempts to find a best fit between the two signals by minimizing small differences and enhancing significant differences. Utilizing this technique, if the sum of all variations between the signals at a number of specified test points (selected frequencies along the horizontal line) is less than some predefined number, then the two signals represent the same person. If the sum of those variations is greater than that predefined number, then R 700 represents a different person than S 800.

However, as noted above, some variations between the signals are meaningful and some are not, so the preferred embodiment of the present invention does not rely upon filtering or the least squares technique alone to determine whether or not R 700 is S 800. As further illustrated in FIG. 8, a horizontal relevancy line 850 has been added below the spectrogram 800. The relevancy line provides an indication of the relevancy of different portions of spectrogram 800 toward the positive or negative identification of a person scanned. The relevancy line 850, as illustrated in FIG. 8, is comprised of three types of regions, forward slash regions 852, blank regions 854, and backward slash regions 856. Only three types of regions are shown in FIG. 8 for purposes of simplifying the drawing, but as many regions as were necessary could be utilized.

Forward slash regions 852 correspond to regions of lower relevance, meaning that there can be a bigger difference between the amplitude in decibels of a point ($f_1$) at a particular frequency on R 700 within region 852 from the amplitude of a point ($f_2$) at that same frequency on S 800. For purposes of simplicity, this difference is referred to as $\Delta$, which is the difference between $f_1$ and $f_2$. Hence, the forward slash regions 852 would have a higher threshold level that $\Delta$ would have to exceed before a variation between R 700 and S 800 was considered to be meaningful. Blank regions 854 correspond to regions of high relevance and therefore have a low threshold level for $\Delta$. Backward slash regions 856 correspond to regions of medium relevance and therefore have a threshold level for $\Delta$ between that of blank regions 854 and forward slash regions 852.

Figure 9:
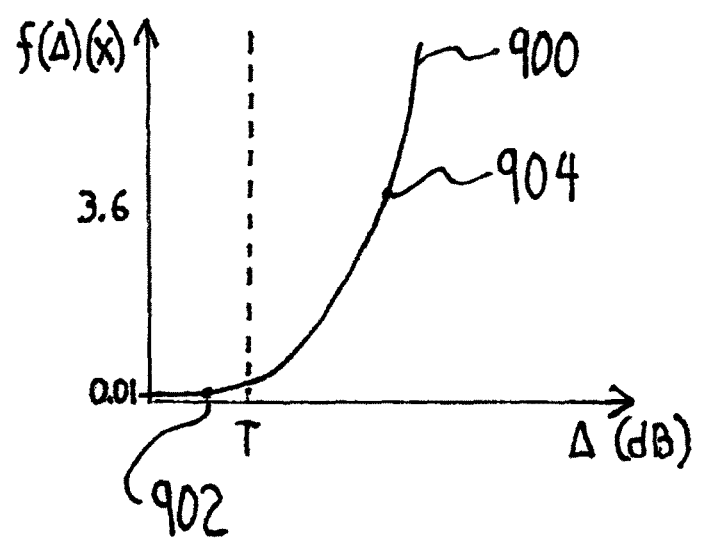
FIG. 9 is an illustration of a filtering analysis in accordance with a preferred embodiment of the present invention.

Furthermore, merely exceeding the threshold for $\Delta$ within a particular region may or may not be significant depending on the particular frequency level and the region involved. This rule is further illustrated with reference now to FIG. 9, which shows a graph of $\Delta$ compared to $f(\Delta)$. The vertical axis $f(\Delta)$ represents values (x) that are assigned to $\Delta$ based on $\Delta$'s position on the line 900, which is a graph of all possible $\Delta$s for that particular point on the spectrograms 700 and 800. As shown, the line T on the horizontal line $\Delta$ represents the threshold for a point within a region of the spectrograms 700 and 800. When it is known that R 700 and S 800 correspond to the same person, a point 902 on line 900 would be expected to be below the threshold T and would therefore be assigned a low $f(\Delta)$ value, in this case the arbitrarily assigned value of 0.01(x). However, if a point 904 is at a much higher point on the line 900, i.e., further past the threshold T, it is assigned a much higher $f(\Delta)$ value, in this case the arbitrarily assigned value of 3.6(x). Since the probability of R 700 belonging to the same person represented by S 800 goes down the further $\Delta$ is past the threshold T, the values $f(\Delta)$ increase exponentially along the vertical line $f(\Delta)$ so as to assign higher and higher values to higher $\Delta$ values.

As with the sum error squared technique described above, the $f(\Delta)$ valuations for each test point on the spectrograms 700 and 800 can also be summed, with the result effectively being a filtered sum. If the filtered sum for R 700 versus S 800 exceeds a predefined number, then R 700 represents a different person than S 800, and if the filtered sum is below that predefined number, then R 700 and S 800 represent the same person. The predefined number itself is not significant because it depends entirely on the values assigned to $f(\Delta)$, which can be arbitrary. Hence, the numbers for $f(\Delta)$ in FIG.

9 are for illustration purposes only and could be readily changed without departing from the teachings of the present invention.

Figure 10:
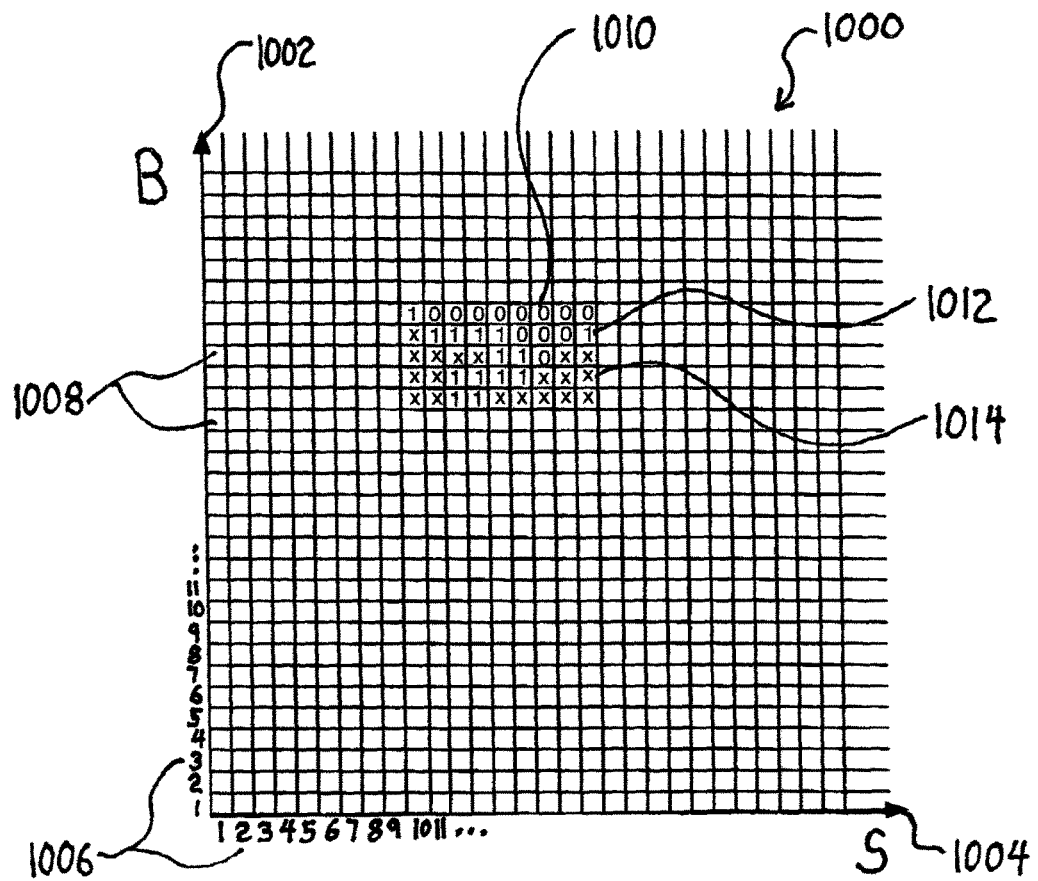
FIG. 10 is an illustration of a personal identity determinator (PID) in accordance with a preferred embodiment of the present invention.

An additional technique to be utilized when comparing spectrograms 700 and 800 is illustrated in FIG. 10, which partially depicts a visual pattern matching technique in accordance with a preferred embodiment of the present invention, referred to herein as a personal identity determinator (PID). FIG. 10 is a PID graph 1000 of B, a baseline spectrogram, versus S 800, where B is the vertical axis 1002 and S is the horizontal axis 1004. The baseline spectrogram B could be formed in a number of different manners, such as forming B from the mean or median of all spectrograms of a large population of people. The points 1006 along B and S represent the sampling points on each spectrogram. While only a limited number of such points 1006 are represented in the PID graph 1000, the total number of points 1006 could be any number. For example, as noted above when discussing the number of sampling points preferred in a frequency range from 100 MHz to 12 GHz, a total of 3201 sampling points could be used for both B and S, resulting in a 3201×3201 matrix of over ten million sampling points.

However, utilizing that many sampling points in a PID graph will require a significant amount of computing power, memory and processing time, so it is preferable to use between two and three hundred points 1006, representing the approximate number of peaks and valleys in a typical biometric spectrogram for most people. Given the impracticality of representing hundreds of sampling points for both B and S in the PID graph 1000 of FIG. 10, only thirty or so sampling points 1006 are therein illustrated for both B and S. Accordingly, not all of the resulting sampled point squares 1008, representing the crossing points between the same sample points along B and S are illustrated, and only a handful of the sampled point squares 1008 are filled in with a "0" 1010, a "1" 1012 or an "x" 1014, as further described below.

For each sampled point square 1008, a comparison is done between the value of a sampled point 1006 on the spectrogram B 700 and the value of the same sampled point 1006 on the spectrogram S 800. If the value of B for a first sample point is greater than the value of S for the same sample point by more than a threshold level (B>>S), then the corresponding sampled point square 1008 is assigned a "0" value. If the value of B for a first sample point is greater than the value of S for the same sample point by less than a threshold level (B>S), then the corresponding sampled point square 1008 is assigned an "x" value. If the value of B for a first sample point is less than the value of S for the same sample point by less than a threshold level (B<S), then the corresponding sampled point square 1008 is assigned an "x" value. If the value of B for a first sample point is less than the value of S for the same sample point by more than a threshold level (B>>S), then the corresponding sampled point square 1008 is assigned a "1" value.

Whether a sampled point square 1008 is assigned a "0" 1010 or a "1" 1012 value because B is greater or less than S by more than the threshold is not critical. What is important is that sampled point squares 1008 are thrown out or assigned an "x" 1014 value when B is greater or less than S by less than the threshold. This is important because small differences between the values of B and S could result from noise, thereby making those differences unreliable.

Once all of the sampled point squares 1008 have been filled in, a pattern will emerge of 0's, 1's and x's that is unique to that PID graph 1000. The pattern of the B versus S PID graph 1000 can then be stored and compared to a real-time created PID graph corresponding to person P, using B versus R, to see how closely the two PID graphs match. These patterns could be compared using any of a number of well known pattern matching techniques. The closer the proximity between the patterns of 0's, 1's and x's on the two PID graph, the greater the likelihood that R and S correspond to the same person.

Figure 11:
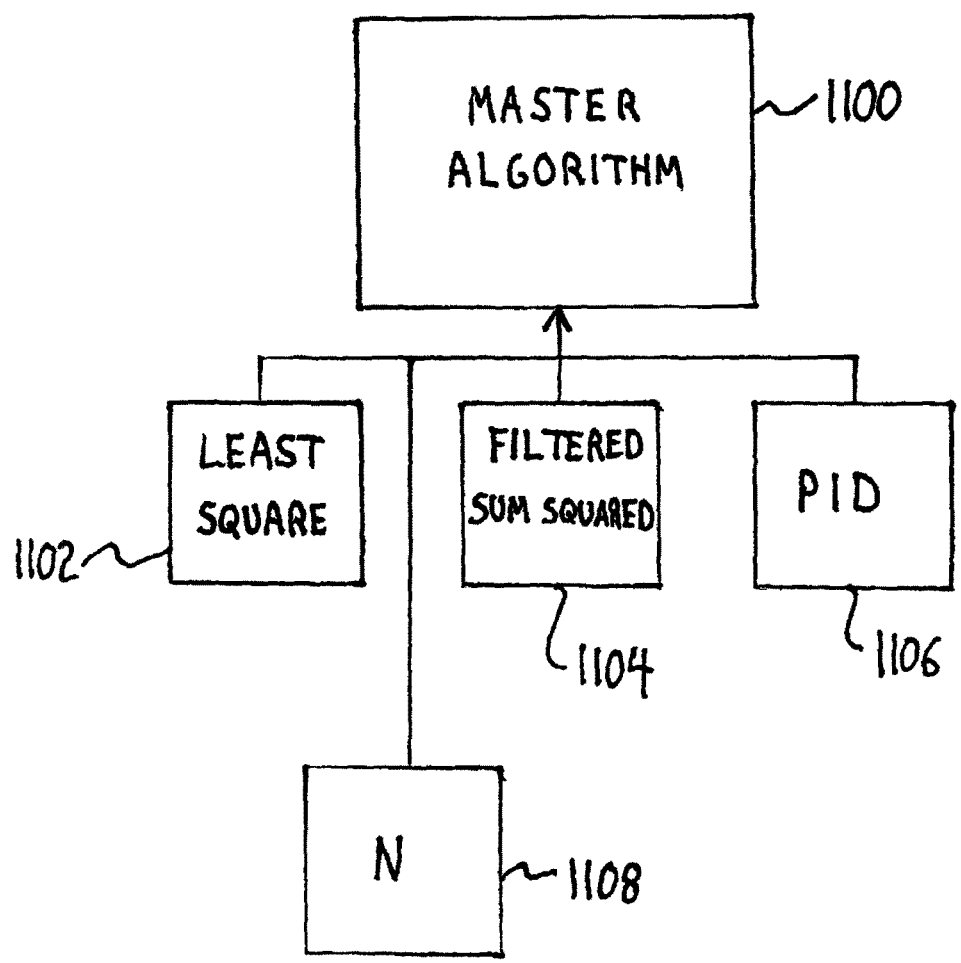
FIG. 11 is a block diagram illustrating the master biometric identification algorithm and its sub-element algorithms.

Although three different methods of comparing 700 to 800 have been discussed, many additional methods are possible. To some extent, the more comparison methods utilized, the higher the reliability of the biometric identification application. Of course, some comparison methods are more significant than others, so it is preferred that a master biometric identification algorithm be utilized with each of the comparison methods as its sub-element algorithms to factor in which sub-element algorithms should be utilized in making a biometric identification and what degree of importance those sub-element algorithms should play in the overall identification determination. As illustrated in FIG. 11, the least square comparison 1102 could be one sub-element to the master algorithm 1100, while the filtered sum square comparison 1104 could be another sub-element, and the PID 1106 could be the next. As denoted by N 1108, any number of additional sub-elements could also be utilized in place of or in addition to those illustrated.

As previously noted, the present invention can be utilized to perform many different tasks or applications. The detection and analysis method to be used in each instance will vary according to the task. For example, scans for human blood components would typically use detection and analysis methods similar to those used to scan for blood sugar levels, but could also use one or more of the methods used for biometric identification, where a known stored signal is compared to a real-time signal. These same types of methods could be used for agricultural inspection, food processing operations, security applications, environmental testing, manufacturing operations and many other applications. Authenticity applications would also be possible, where a security marker is used to mark and subsequently identify a valuable object.

The present invention, while illustrated and described in terms of a preferred embodiment and several alternatives, is not limited to the particular description contained in this specification. Additional alternative or equivalent components and steps could be used to practice the present invention.

What is claimed is:

1. A portable sample scanning and analysis system comprising:
    a sample housing including a human finger-sized housing for holding a sample to be scanned;
    a scanner for scanning the sample, the scanner including a transmitter for transmitting a series of electromagnetic signals, each of the electromagnetic signals having a transmitted amplitude over a plurality of sample points within a range of frequencies, and a receiver for receiving the series of electromagnetic signals as the series of electromagnetic signals are reflected from or transmitted through the sample at substantially the same time as the series of electromagnetic signals are being transmitted, and generating a series of spectral data sets representing at least a scanned amplitude of each of the electromagnetic signals over the plurality of sample points;
    magnets that produce a non-varying magnetic field around any portion of the sample to be scanned, the magnetic field representing substantially all of the magnetic field applied by the system around the sample at the same time the electromagnetic signals are transmitted and received, the transmitter and the receiver being held by the human finger-sized housing on either side of the sample and in close proximity to the magnets and the sample; and an analyzer including a memory and a processor for generating one or more composite spectrograms from the series of spectral data sets, analyzing the composite spectrograms to recognize one or more patterns within the composite spectrograms representing one or more characteristics of the sample, and making a determination regarding the characteristics based on the patterns.

2. The system of claim 1, wherein the sample housing includes at least one node connected to the transmitter and the receiver, the node being held in a fixed position relative to the sample.

3. The system of claim 2, wherein the sample housing further includes a base formed from a dielectric material having a low dissipation factor in which the sample is positioned for scanning, and wherein the housing forms a shield around at least a portion of the base.

4. The system of claim 2, wherein the shape, orientation and material composition of the node is selected to enhance the composite spectrograms.

5. The system of claim 2, wherein the sample housing includes a transmitter node connected to the transmitter and a receiver node connected to the receiver and a base formed to hold the transmitter node and the receiver node in physical contact with the sample.

6. The system of claim 1, wherein the sample housing includes a transmitter node connected to the transmitter and a receiver node connected to the receiver, and wherein the receiver node only receives the series of signals transmitted from the transmitter node.

7. The system of claim 1, wherein the sample housing includes one or more transmitter nodes connected to the transmitter and one or more receiver nodes connected to the receiver, and wherein a single transmitter node corresponds to the one or more receiver nodes that each receives the series of signals transmitted from the single transmitter node.

8. The system of claim 1, wherein the sample housing includes a transmitter node connected to the transmitter and a receiver node connected to the receiver and a base formed to hold the transmitter node and the receiver node in fixed positions relative to the sample, and wherein magnets include one or more pairs of magnets.

9. The system of claim 8, wherein the shape, orientation, strength and material composition of the pairs of magnets are selected to enhance the composite spectrograms.

10. The system of claim 9, wherein the number of pairs of magnets is selected to enhance the composite spectrograms.

11. The system of claim 8, wherein the pairs of magnets are permanent magnets.

12. The system of claim 8, wherein the pairs of magnets are nonpermanent magnets.

13. The system of claim 1, wherein the transmitted amplitude for each of the signals is approximately the same.

14. The system of claim 1, wherein the transmitted amplitude for each of the signals varies.

15. The system of claim 1, wherein the range of frequencies is from approximately 9 KHz to approximately 810 THz.

16. The system of claim 1, wherein the sample is a human finger and wherein the characteristic is a naturally occurring blood component.

17. The system of claim 16, wherein the blood component is glucose, wherein the range of frequencies is from approximately 100 MHz to approximately 3 GHz, and wherein the determination regarding the characteristics is a blood glucose level.

18. The system of claim 1, wherein the sample is a human finger and wherein the characteristic is an introduced blood component.

19. The system of claim 1, wherein the sample is a human finger, wherein the characteristics are biometric markers associated with the human body part, and wherein the determination regarding the characteristics is a positive or negative biometric identity match.

20. The system of claim 19, wherein the range of frequencies is from approximately 10 MHz to approximately 12 GHz.

21. The system of claim 1, wherein the sample housing and at least a portion of the scanner are situated within a unit physically separated from the analyzer, wherein the analyzer communicates the determination regarding the characteristics to the unit, and wherein the unit includes a display capable of displaying the determination regarding the characteristics.

22. The system of claim 21, wherein the unit is wirelessly in communication with the analyzer.

23. The system of claim 21, wherein the analyzer is operative to transmit additional information to the unit based on one or more of the following: the sample, the determination, the characteristic.

24. The system of claim 1, wherein the patterns within the composite spectrums include specific peaks and valleys, representative variations in the composite spectrograms at particular frequencies, and a distance of specific points on the composite spectrograms from a baseline position within the composite spectrograms.

25. The system of claim 1, wherein the sample is a human finger, wherein the characteristic is blood glucose, wherein the determination regarding the characteristics is a blood glucose level, and wherein the patterns within the composite spectrums include a baseline position that correlates with a normal glucose level in humans, a low point, a variation pattern based on movements and variations in the human finger, and a trough formed by the low point.

26. The system of claim 25, wherein the patterns further include a fine-tuning pattern that improves the determination of the blood glucose level in some humans.

27. The system of claim 1, wherein the sample is a human finger, wherein the characteristic is one or more blood components of a human having the human finger, and wherein the analyzer requires no additional information regarding the human to make the determination regarding the characteristics.

28. The system of claim 1, wherein the sample is a human finger, wherein the characteristic is one or more blood components of a human having the human finger, and wherein the determination regarding the characteristic is weight information regarding the human.

29. The system of claim 28, wherein the memory and the processor of the analyzer further obtains caloric intake and expenditure information from the human to assist the analyzer in making the determination.

30. The system of claim 1, wherein the sample is a human finger, wherein the characteristics are biometric markers associated with the human finger, wherein the patterns within the composite spectrograms are matched to one or more pre-existing patterns within one or more pre-existing composite spectrograms for one or more humans, and wherein the determination regarding the characteristics is a positive or negative biometric identity match based on whether the patterns within the composite spectrograms match one or more of the patterns within one or more of the pre-existing composite spectrograms.

31. The system of claim 30, wherein the composite spectrograms and the pre-existing spectrograms have been processed by the analyzer to reduce dynamic variances prior to making the determination.

32. The system of claim 31, wherein the analyzer reduces dynamic variances using one or more of the following: a filtered sum comparison, a personal identity determinator matrix, a least squares error estimation.

33. The system of claim 30, wherein the composite spectrograms and the pre-existing spectrograms have been processed by the analyzer to create one or more filtered composite spectrograms in which dynamic variances have been reduced prior to making the determination using one or more of the following: a filtered sum comparison, a personal identity determinator matrix, a least squares error estimation.

34. The system of claim 33, wherein the analyzer further analyzes each of the filtered composite spectrograms to factor in a degree of accuracy that each of the filtered composite spectrograms adds to the determination.

35. The system of claim 1, wherein the sample is a food product, wherein the characteristics are one or more conditions of the food product, and wherein the determination regarding the characteristics is a suitability of the food product for human consumption.

36. The system of claim 1, wherein the sample is a food product, wherein the characteristics are one or more conditions of the food product, and wherein the determination regarding the characteristics is an ingredient mixture of the food product.

37. The system of claim 1, wherein the characteristic is the presence of a controlled or unwanted substance within the sample, and wherein the determination regarding the characteristics is an identification of the presence of the substance.

38. The system of claim 1, wherein the sample is taken from air, water or ground, wherein the characteristics are a presence of one or more substances within the sample, and wherein the determination regarding the characteristics is an identification of the presence of the substances.

39. The system of claim 1, wherein the sample is a manufacturing material, wherein the characteristics are a presence of one or more substances within the sample, and wherein the determination regarding the characteristics is an identification of the presence or consistency of the substances.

40. The system of claim 39, wherein the manufacturing material is an output of a manufacturing operation.

41. The system of claim 39, wherein the manufacturing material is exhaust or effluent.

42. The system of claim 39, wherein the substances are one or more byproducts.

43. The system of claim 1, wherein the sample is a liquid, and wherein the characteristics are a composition of the liquid.

44. The system of claim 43, wherein the liquid is an identified liquid, wherein the determination regarding the characteristics is an indication of whether the liquid is the identified liquid.

45. The system of claim 1, wherein the sample is a valuable object, wherein the characteristics are one or more security markers identifying the valuable object, and wherein the determination regarding the characteristics is an indication of whether the security markers are present and appropriately correspond to the valuable object.

46. A portable sample scanning and analysis system comprising:
a sample housing having a human finger-sized housing for holding a sample to be scanned, including a base for positioning and orienting the sample and one or more pairs of magnets positioned so as to create a non-varying magnetic field surrounding at least a portion of the sample;
a scanner for scanning the sample, the scanner including a transmitter having one or more transmitter nodes for transmitting a series of electromagnetic signals, each of the electromagnetic signals having a transmitted amplitude over a plurality of sample points within a range of frequencies, and a receiver having one or more receiver nodes for receiving the series of electromagnetic signals as the series of electromagnetic signals are reflected from or transmitted through the sample at substantially the same time as the series of electromagnetic signals are being transmitted and generating a series of spectral data sets representing at least a scanned amplitude of each of the electromagnetic signals over the plurality of sample points, the sample housing being formed to hold the transmitter nodes and the receiver nodes on either side of the sample and in fixed positions relative to the sample, the magnetic field further surrounding the transmitter nodes and the receiver nodes, wherein the magnetic field represents substantially all of the magnetic field applied by the system around the sample at the same time the electromagnetic signals are transmitted and received; and
an analyzer including a memory and a processor for generating one or more composite spectrograms from the series of spectral data sets, analyzing the composite spectrograms to recognize one or more patterns within the composite spectrograms representing one or more characteristics of the sample, and making a determination regarding the characteristics based on the patterns.

47. The system of claim 46, wherein the base is formed from a dielectric material having a low dissipation factor.

48. The system of claim 46, wherein the housing that forms a shield around at least a portion of the base.

49. The system of claim 46, wherein a single transmitter node corresponds to a single receiver node that only receives the series of signals transmitted from the single transmitter node.

50. The system of claim 46, wherein a single transmitter node corresponds to one or more receiver nodes that each receives the series of signals transmitted from the single transmitter node.

51. The system of claim 46, wherein the shape, orientation and material composition of the transmitter nodes and the receiver nodes are selected to enhance the composite spectrograms' representation of one or more characteristics of the sample.

52. The system of claim 46, wherein the base is formed to hold the transmitter nodes and the receiver nodes in physical contact with the sample.

53. The system of claim 46, wherein the shape, orientation, strength and material composition of the pairs of magnets are selected to enhance the composite spectrograms.

54. The system of claim 46, wherein the number of pairs of magnets is selected to enhance the composite spectrograms.

55. The system of claim 46, wherein the pairs of magnets are permanent magnets.

56. The system of claim 46, wherein the pairs of magnets are nonpermanent magnets.

57. The system of claim 46, wherein the transmitted amplitude for each of the signals is approximately the same.

58. The system of claim 46, wherein the transmitted amplitude for each of the signals varies.

59. The system of claim 46, wherein the range of frequencies is from approximately 9 KHz to approximately 810 THz.

60. The system of claim 46, wherein the sample is a human finger and wherein the characteristic is a naturally occurring blood component.

61. The system of claim 60, wherein the blood component is glucose, wherein the range of frequencies is from approximately 100 MHz to approximately 3 GHz, and wherein the determination regarding the characteristics is a blood glucose level.

62. The system of claim 46, wherein the sample is a human finger and wherein the characteristic is an introduced blood component.

63. The system of claim 46, wherein the sample is a human finger, wherein the characteristics are biometric markers associated with the human finger, and wherein the determination regarding the characteristics is a positive or negative biometric identity match.

64. The system of claim 63, wherein the range of frequencies is from approximately 10 MHz to approximately 12 GHz.

65. The system of claim 46, wherein the sample housing and at least a portion of the scanner modulo are situated within a unit physically separated from the analyzer, wherein the analyzer communicates the determination regarding the characteristics to the unit, and wherein the unit includes a display capable of displaying the determination regarding the characteristics.

66. The system of claim 65, wherein the unit is wirelessly in communication with the analyzer.

67. The system of claim 65, wherein the analyzer is operative to transmit additional information to the unit based on one or more of the following: the sample, the determination, the characteristic.

68. The system of claim 46, wherein the patterns within the composite spectrums include specific peaks and valleys, representative variations in the composite spectrograms at particular frequencies, and a distance of specific points on the composite spectrograms from a baseline position within the composite spectrograms.

69. The system of claim 46, wherein the sample is a human finger, wherein the characteristic is blood glucose, wherein the determination regarding the characteristics is a blood glucose level, and wherein the patterns within the composite spectrums include a baseline position that correlates with a normal glucose level in humans, a low point, a variation pattern based on movements and variations in the human finger, and a trough formed by the low point.

70. The system of claim 69, wherein the patterns further includes a fine-tuning pattern that improves the determination of the blood glucose level in some humans.

71. The system of claim 46, wherein the sample is a human finger, wherein the characteristic is one or more blood components of a human having the human finger, and wherein the analyzer requires no additional information regarding the human to make the determination regarding the characteristics.

72. The system of claim 46, wherein the sample is a human finger, wherein the characteristic is one or more blood components of a human having the human finger, and wherein the determination regarding the characteristic is weight information regarding the human.

73. The system of claim 72, wherein the memory and the processor of the analyzer further obtains caloric intake and expenditure information from the human to assist the analyzer in making the determination.

74. The system of claim 46, wherein the sample is a human finger, wherein the characteristics are biometric markers associated with the human finger, wherein the patterns within the composite spectrograms are matched to one or more pre-existing patterns within one or more pre-existing composite spectrograms for one or more humans, and wherein the determination regarding the characteristics is a positive or negative biometric identity match based on whether the patterns within the composite spectrograms match one or more of the patterns within one or more of the pre-existing composite spectrograms.

75. The system of claim 74, wherein the composite spectrograms and the pre-existing spectrograms have been processed by the analyzer to reduce dynamic variances prior to making the determination.

76. The system of claim 75, wherein the analyzer reduces dynamic variances using one or more of the following: a filtered sum comparison, a personal identity determinator matrix, a least squares error estimation.

77. The system of claim 74, wherein the composite spectrograms and the pre-existing spectrograms have been processed by the analyzer to create one or more filtered composite spectrograms in which dynamic variances have been reduced prior to making the determination using one or more of the following: a filtered sum comparison, a personal identity determinator matrix, a least squares error estimation.

78. The system of claim 77, wherein the analyzer further analyzes each of the filtered composite spectrograms to factor in a degree of accuracy that each of the filtered composite spectrograms adds to the determination.

79. The system of claim 46, wherein the sample is a liquid, and wherein the characteristics are a composition of the liquid.

80. The system of claim 79, wherein the liquid is alleged to be a specific type of liquid, and wherein the determination regarding the characteristics is an authentication of the specific liquid.

81. The system of claim 46, wherein the sample is a valuable object, wherein the characteristics are one or more security markers identifying the valuable object, and wherein the determination regarding the characteristics is an indication of whether the security markers are present and appropriately correspond to the valuable object.

82. A method for scanning and analyzing a sample, comprising the steps of:
receiving the sample within a human finger-sized housing of a sample housing of a portable device for scanning and analysis;
scanning the sample by transmitting a series of electromagnetic signals generated by a transmitter, each of the electromagnetic signals having a transmitted amplitude over a plurality of sample points within a range of frequencies, and receiving at substantially the same time as the series of signals are being transmitted each of the electromagnetic signals with a receiver as the electromagnetic signals are reflected from or transmitted through the sample in a non-varying magnetic field that surrounds any portion of the sample to be scanned, the magnetic field representing substantially all of the applied magnetic field at the same time the electromagnetic signals are transmitted and received, wherein the transmitter and the receiver are position on either side of and in close proximity to the sample;

generating a series of spectral data sets representing at least a scanned amplitude of each of the electromagnetic signals over the plurality of sample points;

generating a composite spectrogram from the series of spectral data sets;

analyzing the composite spectrogram to recognize one or more patterns within the composite spectrogram representing a characteristic of the sample; and making a determination regarding the characteristic based on the patterns.

83. The method of claim 82, wherein the step of scanning includes the step of transmitting the series of signals through one or more transmitter nodes within the sample housing and receiving each of the signals with one or more receiver nodes within the sample housing.

84. The method of claim 83, wherein the step of scanning includes the step of shaping and orienting the transmitter nodes and the receiver nodes to enhance the composite spectrogram.

85. The method of claim 83, wherein the step of receiving includes the step of aligning the sample to physically contact the transmitter nodes and the receiver nodes.

86. The method of claim 83, wherein the step of receiving includes the step of positioning a pair of magnets to create the magnetic field.

87. The method of claim 86, wherein the step of receiving further includes shaping and orienting the pair of magnets to enhance the composite spectrogram.

88. The method of claim 82, wherein the step of scanning includes the step of transmitting the series of signals through a single transmitter node and receiving each of the signals with a single receiver node.

89. The method of claim 82, wherein the step of scanning includes the step of transmitting the series of signals through two or more transmitter nodes and receiving each of the signals with a single receiver node.

90. The method of claim 82, wherein the transmitted amplitude for each of the signals is approximately the same.

91. The method of claim 82, wherein the transmitted amplitude for each of the signals varies.

92. The method of claim 82, wherein the range of frequencies is from approximately 9 KHz to approximately 810 THz.

93. The method of claim 82, wherein the sample is a human body part and wherein the characteristic is a naturally occurring blood component.

94. The method of claim 93, wherein the blood component is glucose, wherein the range of frequencies is from approximately 100 MHz to approximately 3 GHz, and wherein the determination regarding the characteristic is a blood glucose level.

95. The method of claim 82, wherein the sample is a human body part and wherein the characteristic is an introduced blood component.

96. The method of claim 82, wherein the sample is a human body part, wherein the characteristics are biometric markers associated with the human body part, and wherein the determination regarding the characteristic is a positive or negative biometric identity match.

97. The method of claim 96, wherein the range of frequencies is from approximately 10 MHz to approximately 12 GHz.

98. The method of claim 82, wherein the steps of receiving, scanning and generating a series of spectral data sets are performed in a first location, wherein the steps of generating a composite, analyzing and making are performed in a second location, and further comprising the step of displaying the determination regarding the characteristic.

99. The method of claim 98, wherein the step of displaying is performed in the first location.

100. The method of claim 99, further comprising the steps of:

communicating the series of spectral data sets from the first location to the second location; and communicating the determination regarding the characteristic from the second location to the first location.

101. The method of claim 100, further comprising the step of communicating additional information from the second location to the first location based on one or more of the following: the sample, the determination, the characteristic.

102. The method of claim 82, wherein the patterns include specific peaks and valleys, representative variations in the composite spectrogram at particular frequencies, and one or more distances from specific points on the composite spectrogram to a baseline position within the composite spectrogram.

103. The method of claim 82, wherein the sample is a human body part, wherein the characteristic is blood glucose, wherein the determination regarding the characteristics is a blood glucose level, and wherein the patterns within the composite spectrums include a baseline position that correlates with a normal glucose level in humans, a low point, a variation pattern based on movements and variations in the human body part, and a trough formed by the low point.

104. The method of claim 103, wherein the step of analyzing the composite spectrogram further includes the step of recognizing a fine-tuning pattern that improves the determination of the blood glucose level in some humans.

105. The method of claim 82, wherein the sample is a human body part, wherein the characteristic is one or more blood components of a human having the human body part, and wherein the step of making a determination requires no additional information regarding the human to make the determination regarding the characteristic.

106. The method of claim 82, wherein the sample is a human body part, wherein the characteristic is one or more blood components of a human having the human body part, and wherein the determination regarding the characteristic is weight information regarding the human.

107. The method of claim 106, wherein the step of making the determination includes obtaining caloric intake and expenditure information from the human.

108. The method of claim 82, wherein the sample is a human body part, wherein the characteristic is a biometric marker associated with the human body part, wherein the patterns within the composite spectrogram are matched to one or more pre-existing patterns within one or more pre-existing composite spectrograms for one or more humans, and wherein the determination regarding the characteristics is a positive or negative biometric identity match based on whether the patterns within the composite spectrogram matches one or more of the patterns within one or more of the pre-existing composite spectrograms.

109. The method of claim 108, wherein the step of generating a composite spectrogram includes the step of reducing dynamic variances in the composite spectrogram.

110. The method of claim 109, wherein the step of reducing dynamic variances uses one or more of the following: a filtered sum comparison, a personal identity determinator matrix, a least squares error estimation.

111. The method of claim 108, wherein the step of generating a composite spectrogram includes the step of filtering the composite spectrogram to reduce dynamic variances using one or more of the following: a filtered sum comparison, a personal identity determinator matrix, a least squares error estimation.

112. The method of claim 111, wherein the step of analyzing further includes the step of factoring in a degree of accuracy that a filtered composite spectrogram adds to the determination.

* * * * *